United States Patent
Rabbani et al.

(10) Patent No.: US 12,044,684 B2
(45) Date of Patent: Jul. 23, 2024

(54) METHODS FOR DIAGNOSING AN AUTISTIC SPECTRUM DISORDER

(71) Applicant: QATAR UNIVERSITY, Doha (QA)

(72) Inventors: Naila Rabbani, Warwickshire (GB); Paul J. Thornalley, Warwickshire (GB); Kashif Mahmood Rajpoot, Birmingham (GB); Marina Marini, Bologna (IT); Provvidenza Maria Abruzzo, Bologna (IT); Alessandra Bolotta, Bologna (IT)

(73) Assignee: QATAR UNIVERSITY, Doha (QA)

( * ) Notice: Subject to any disclaimer, the term of this patent is extended or adjusted under 35 U.S.C. 154(b) by 1024 days.

(21) Appl. No.: 16/967,361

(22) PCT Filed: Feb. 11, 2019

(86) PCT No.: PCT/GB2019/050362
§ 371 (c)(1),
(2) Date: Aug. 4, 2020

(87) PCT Pub. No.: WO2019/155233
PCT Pub. Date: Aug. 15, 2019

(65) Prior Publication Data
US 2021/0033621 A1 Feb. 4, 2021

(30) Foreign Application Priority Data
Feb. 9, 2018 (GB) ..................................... 1802116

(51) Int. Cl.
*G01N 33/68* (2006.01)
(52) U.S. Cl.
CPC ..... *G01N 33/6848* (2013.01); *G01N 2800/30* (2013.01); *G01N 2800/52* (2013.01)

(58) Field of Classification Search
None
See application file for complete search history.

(56) References Cited

U.S. PATENT DOCUMENTS

| 2007/0238761 A1 | 10/2007 | Hudson et al. |
| 2010/0210582 A1 | 8/2010 | Stewart et al. |

FOREIGN PATENT DOCUMENTS

| JP | 2014/506244 A | 3/2014 |
| WO | WO 2006/090185 A1 | 8/2006 |
| WO | WO 2011/139914 A1 | 11/2011 |

OTHER PUBLICATIONS

International Search Report and Written Opinion issued in PCT International Patent Application No. PCT/GB2019/050362, dated Apr. 6, 2019.

(Continued)

*Primary Examiner* — Xiaoyun R Xu
(74) *Attorney, Agent, or Firm* — SQUIRE PATTON BOGGS (US) LLP

(57) ABSTRACT

The present invention provides methods for diagnosing an autistic spectrum disorder (ASD), comprising detecting the concentration of an amino acid adduct in a sample obtained from a subject, wherein said amino acid adduct is a glycated amino acid adduct, an oxidised amino acid adduct, or a nitrated amino acid adduct. Methods of the invention further comprise comparing the concentration of the amino acid adduct in the sample with the concentration of the same amino acid adduct in a reference standard; and identifying the presence or absence of a concentration difference of said amino acid adduct in the sample relative to the reference standard; wherein the presence or absence of a concentration difference correlates with the presence or absence of ASD. Diagnostic algorithms for use in methods of the invention are also provided.

18 Claims, 29 Drawing Sheets

(56) References Cited

OTHER PUBLICATIONS

Attia Anwar et al., "Advanced glycation endproducts, dityrosine and arginine transporter dysfunction in autism—a source of biomarkers for clinical diagnosis", Molecular Autism, vol. 9, No. 1, Feb. 19, 2018.
Mona Mohamed Zaki et al., "Assessment of plasma amino acid profile in autism using cation-exchange chromatography with postcolumn derivatization by ninhydrin", Turkish Journal of Medical Sciences, vol. 47, Jan. 1, 2017, pp. 260-267.
Alessandro Ghezzo et al., "Oxidative Stress and Erythrocyte Membrane Alterations in Children with Autism: Correlation with Clinical Features", PLOS One, vol. 8, No. 6, Jun. 19, 2013.
Mohammed A. Junaid et al., "Proteomic studies identified a single nucleotide polymorphism in glyoxalase I as autism susceptibility factor", American Journal of Medical Genetics, vol. 131, No. 1, Nov. 15, 2004.
Attia Anwar et al., "Quantitation of plasma thiamine, related metabolites and plasma protein oxidative damage markers in children with autism spectrum disorder and healthy controls", Free Radical Research, vol. 50 sup1, Nov. 1, 2016.
International Search Report and Written Opinion dated Apr. 6, 2019 for Application No. PCT/GB2019/050362; 5 pages.
Written Opinion of the International Searching Authority dated Apr. 6, 2019 for Application No. PCT/GB2019/050362; 12 pages.
Search Report Under Rule 17(5) dated Oct. 8, 2018 for Application No. GB1802116.2; 6 pages.
Communication Under Rule 164(2)(a) EPC dated Jun. 10, 2022 for Application No. EP19705995.9; 7 pages.
Ahmed, et al: "Biomarkers of early stage osteoarthritis, rheumatoid arthritis and musculoskeletal health", Scientific Reports; Mar. 19, 2015; vol. 5(9259).
Anwar, et al: "Advanced glycation endproducts, dityrosine and arginine transporter dysfunction in autism—a source of biomarkers for clinical diagnosis", Molecular Autism; Feb. 19, 2018; vol. 9(1), the whole document.
Anwar, et al: "Quantitation of plasma thiamine, related metabolites and plasma protein oxidative damage markers in children with autism spectrum disorder and healthy controls", Free Radical Research 2016; vol. 50(1), pp. S85-S90.
Dieme, et al: "Metabolomics study of urine in autism spectrum disorders using a multiplatform analytical methodology", Journal of Proteome Research 2015; vol. 14(12), pp. 5273-5282.
Ghezzo, et al: "Oxidative stress and Erythrocyte membrane alterations in children with autism: Correlation with clinical features", PLOS One; Jun. 19, 2013; vol. 8(6), p. e66418.
Junaid, et al: "Proteomic studies identified a single nucleotide polymorphism in Glyoxalase I as autism susceptibility factor", American Journal of Medical Genetics; Nov. 15, 2004; vol. 131A(1), pp. 11-17.
Ozonoff, et al: "The onset of autism: Patterns of symptom emergence in the first years of life", Autism Research 2008; vol. 1(6), pp. 320-328.
Rabbani, et al: "Assay of methylglyoxal-derived protein and nucleotide AGEs", Biochem Soc Trans 2014; vol. 42(2), pp. 511-517.
Sasaki, et al: "Functional characterization of 5-Oxoproline transport via SLC16A1/MCT1", Journal of Biological Chemistry 2015; vol. 290(4), pp. 2303-2311.
Thornalley & Rabbani: "Detection of oxidized and glycated proteins in clinical samples using mass spectrometry—A user's perspective", Biochimica & Biophysica Acta 2014 (published online Apr. 2, 2013); vol. 1840, pp. 818-829.
Zaki, et al: "Assessment of plasma amino acid profile in autism using cation-exchange chromatography with post-column derivatization by ninhydrin", Turkish Journal of Medical Sciences; May 28, 2016; vol. 47, pp. 260-267.
Notice of Reasons for Refusal drafted Feb. 7, 2023 for Japanese Patent Application No. 2020-541777; with machine translation, 5 pages.
Japanese Office Action issued in corresponding Japanese Patent Application No. 2020-541777 dated Aug. 29, 2023.
European Office Action issued in corresponding European Patent Application No. 19 705 995.9-1118 dated Aug. 16, 2023.
Japanese Office Action issued in corresponding Japanese Patent Application No. 2020-541777 on Feb. 6, 2024.

FIGURE 3

| No | Age - years | Gender | ADOS score | CARS total score | CARS activity level item score (hyperactivity) | CARS body use item score (stereotypes) | CARS total number of items with score ≥ 3 | Autism severity level | Cognitive/ developmental impairment | Onset pattern (1, early; 2, regressive; 3, mixed)† | Probability of autism‡ from algorithm no. | | | |
|---|---|---|---|---|---|---|---|---|---|---|---|---|---|---|
| | | | | | | | | | | | 1 | 2 | 3 | 4 |
| 1 | 6.0 | m | 22 | 41.0 | 2.0 | 3.0 | 9 | severe | severe | 1 | 0.93 | 0.79 | 0.82 | 0.80 |
| 2 | 5.6 | m | 14 | 34.0 | 2.0 | 2.0 | 2 | mild | mild | 1 | 1.00 | 0.71 | 0.99 | 0.77 |
| 3 | 5.5 | m | 18 | 40.5 | 2.5 | 3.5 | 9 | severe | moderate | 1 | 1.00 | 0.86 | 1.00 | 0.29 |
| 4 | 5.4 | f | 17 | 31.5 | 2.0 | 2.0 | 1 | mild | mild | 3 | 0.88 | 0.69 | 0.55 | 0.27 |
| 5 | 8.5 | m | 22 | 36.5 | 2.0 | 2.5 | 6 | mild | mild | 3 | 0.98 | 0.64 | 1.00 | 0.88 |
| 6 | 8.7 | m | 19 | 44.5 | 3.0 | 3.0 | 11 | severe | moderate | 2 | 1.00 | 0.69 | 1.00 | 0.74 |
| 7 | 6.8 | m | 19 | 36.5 | 2.5 | 2.0 | 7 | mild | normal IQ | 1 | 1.00 | 0.63 | 1.00 | 0.91 |
| 8 | 5.5 | f | 15 | 41.5 | 2.5 | 2.0 | 9 | severe | borderline IQ | 1 | 0.73 | 0.77 | 0.72 | 0.92 |
| 9 | 11.9 | m | 22 | 44.5 | 2.5 | 3.0 | 11 | severe | severe | 2 | 0.20 | 0.91 | 0.34 | 0.45 |
| 10 | 9.2 | f | 15 | 47.5 | 3.5 | 3.0 | 13 | severe | moderate | 1 | 0.84 | 0.88 | 0.94 | 0.36 |
| 11 | 12.0 | m | 20 | 39.0 | 3.0 | 3.5 | 8 | severe | severe | 3 | 0.94 | 0.68 | 0.82 | 0.63 |
| 12 | 6.2 | m | 22 | 42.5 | 3.0 | 2.5 | 10 | severe | severe | 1 | 1.00 | 0.69 | 1.00 | 0.98 |
| 13 | 6.7 | m | 21 | 40.5 | 2.5 | 3.0 | 9 | severe | severe | 2 | 0.83 | 0.51 | 0.85 | 0.56 |
| 14 | 6.6 | m | 19 | 37.0 | 2.5 | 3.0 | 7 | severe | moderate | 1 | 0.83 | 0.63 | 0.74 | 0.97 |
| 15 | 5.5 | m | 22 | 40.5 | 3.0 | 3.0 | 9 | severe | moderate | 3 | 0.68 | 0.57 | 0.82 | 0.98 |
| 16 | 5.7 | m | 20 | 41.5 | 2.5 | 3.0 | 11 | severe | severe | 1 | 0.98 | 0.81 | 0.98 | 0.81 |

FIGURE 3 (continued)

| No | Age (years) | Gender | ADOS score | CARS total score | CARS activity level item score (hyperactivity) | CARS body use item score (stereotypes) | CARS total number of items with score ≥ 3 | Autism severity level | Cognitive/ developmental impairment | Onset pattern (1, early; 2, regressive; 3, mixed)† | Probability of autism‡ from algorithm no. 1 | 2 | 3 | 4 |
|----|-------------|--------|------------|------------------|------------------------------------------------|----------------------------------------|--------------------------------------------|----------------------|-------------------------------------|------------------------------------------------------|---|---|---|---|
| 17 | 7.8 | m | 21 | 46.0 | 3.5 | 4.0 | 11 | severe | severe | 1 | 0.83 | 0.35 | 0.52 | 0.79 |
| 18 | 5.7 | f | 20 | 43.5 | 2.5 | 3.0 | 10 | severe | normal IQ | 3 | 0.85 | 0.39 | 0.58 | 0.68 |
| 19 | 7.8 | m | 20 | 48.5 | 3.0 | 4.0 | 12 | severe | severe | 2 | 0.95 | 0.58 | 0.93 | 0.57 |
| 20 | 6.8 | m | 19 | 42.0 | 3.0 | 3.0 | 9 | severe | moderate | 2 | 0.67 | 0.61 | 0.54 | 0.77 |
| 21 | 9.6 | m | 19 | 39.5 | 3.0 | 3.0 | 7 | severe | severe | 1 | 0.55 | 0.44 | 0.62 | 0.51 |
| 22 | 6.2 | m | 19 | 41.0 | 2.5 | 3.0 | 9 | severe | severe | 3 | 0.81 | 0.32 | 0.78 | 0.73 |
| 23 | 8.3 | m | 16 | 35.0 | 2.5 | 2.0 | 3 | moderate | moderate | 1 | 0.70 | 0.35 | 0.63 | 0.56 |
| 24 | 7.1 | m | 22 | 41.0 | 2.5 | 2.0 | 7 | severe | moderate | 1 | 0.83 | 1.00 | 0.99 | 1.00 |
| 25 | 6.2 | f | 17 | 38.0 | 2.0 | 2.5 | 7 | severe | severe | 1 | 0.28 | 0.82 | 0.15 | 0.79 |
| 26 | 10.3 | f | 21 | 33.5 | 2.0 | 2.0 | 4 | moderate | normal IQ | 3 | 0.89 | 0.55 | 0.82 | 0.86 |
| 27 | 10.7 | m | 19 | 39.0 | 2.0 | 2.5 | 7 | moderate | normal IQ | 1 | 0.89 | 0.60 | 0.97 | 0.52 |
| 28 | 6.5 | m | 17 | 39.0 | 3.0 | 2.5 | 6 | moderate | normal IQ | 3 | ND | ND | ND | 0.76 |
| 29 | 8.0 | m | 22 | 44.0 | 2.5 | 3.0 | 11 | severe | moderate | 1 | ND | ND | ND | 0.54 |
| 30 | 7.0 | m | 18 | 39.5 | 2.5 | 3.0 | 8 | moderate | normal IQ | 1 | ND | ND | ND | 0.96 |
| 31 | 9.5 | m | 21 | 47.0 | 3.0 | 3.5 | 13 | severe | severe | 1 | ND | ND | ND | 0.29 |
| 32 | 8.6 | m | 16 | 41.5 | 4.0 | 2.0 | 10 | severe | moderate | 3 | ND | ND | ND | 0.33 |
| 33 | 10.9 | m | 18 | 35.0 | 2.0 | 3.0 | 3 | mild | normal IQ | 1 | ND | ND | ND | 0.28 |

FIGURE 3 (continued)

| No | Age (years) | Gender | ADOS score | CARS total score | CARS activity level item score (hyperactivity) | CARS body use item score (stereotypes) | CARS total number of items with score ≥ 3 | Autism severity level | Cognitive/developmental impairment | Onset pattern (1, early; 2, regressive; 3, mixed)† | Probability of autism‡ from algorithm no. 1 | 2 | 3 | 4 |
|---|---|---|---|---|---|---|---|---|---|---|---|---|---|---|
| 34 | 5.8 | f | 18 | 43.0 | 2.5 | 3.0 | 11 | severe | moderate | 2 | ND | ND | ND | 0.30 |
| 35 | 5.3 | f | 17 | 39.5 | 2.5 | 2.5 | 6 | moderate | normal IQ | 1 | ND | ND | ND | 0.62 |
| 36 | 5.3 | f | 17 | 41.0 | 2.5 | 2.5 | 7 | severe | normal IQ | 1 | ND | ND | ND | 0.77 |
| 37 | 8.2 | m | 20 | 41.0 | 2.0 | 3.5 | 9 | severe | moderate | 1 | ND | ND | ND | 0.58 |
| 38 | 11.1 | m | 13 | 34.0 | 2.0 | 1.5 | 2 | mild | normal IQ | 3 | ND | ND | ND | 0.87 |

FIGURE 4

| Glycation markers | Healthy controls | ASD | p-value |
|---|---|---|---|
| FL (mmol/mol lys) | 1.27 ± 0.39 | 1.41 ± 0.53 | NS |
| CML (mmol/mol lys) | 0.158 ± 0.026 | 0.190 ± 0.038 | 0.0018* |
| CEL (mmol/mol lys) | 0.117 ± 0.044 | 0.092 ± 0.054 | NS |
| G-H1 (mmol/mol arg) | 0.012 ± 0.005 | 0.016 ± 0.011 | NS |
| MG-H1 (mmol/mol arg) | 0.473 ± 0.074 | 0.535 ± 0.100 | 0.021 |
| 3DG-H (mmol/mol arg) | 0.165 ± 0.037 | 0.138 ± 0.027 | 0.0052 |
| CMA (mmol/mol arg) | 0.054 (0.043 – 0.067) | 0.077 (0.066 – 0.101) | 0.000082 ** |
| MOLD (mmol/mol lys) | 0.027 ± 0.011 | 0.025 ± 0.016 | NS |
| GSP (mmol/mol lys) | 0.514 ± 0.111 | 0.571 ± 0.206 | NS |
| DT (mmol/mol tyr) | 0.025 (0.019 – 0.031) | 0.047 (0.035 – 0.094) | 0.000012 *** |
| NFK (mmol/mol trp) | 15.6 ± 1.7 | 15.0 ± 1.5 | NS |
| AASA (mmol/mol arg) | 0.154 ± 0.048 | 0.152 ± 0.081 | NS |
| GSA (mmol/mol arg) | 0.639 ± 0.327 | 0.713 ± 0.350 | NS |
| 3-NT (mmol/mol tyr) | 0.0056 (0.0045 – 0.0069) | 0.0053 (0.0045 – 0.0064) | NS |

FIGURE 5

| Amino acid | Plasma (nM) | | p-value |
|---|---|---|---|
| | Healthy controls | ASD | |
| FL | 1489 (987 – 1863) | 751 (361 – 1.570) | 0.047 |
| CML | 807 (587 – 1051) | 853 (219 – 1222) | |
| CEL | 402 (298 – 477) | 420 (310 – 599) | |
| G-H1 | 0.819 (0.553 – 1.26) | 0.527 (0.366 – 0.959) | 0.037 |
| MG-H1 | 271 (176 – 475) | 335 (213 – 500) | |
| 3DG-H | 413 (303 – 637) | 360 (280 – 434) | |
| CMA | 9.18 (6.67 – 12.5) | 17.7 (13.2 – 24.8) | 0.00052** |
| GSP | 12.8 (7.4 – 17.1) | 12.9 (9.3 – 22.0) | |
| MOLD | 1.79 (0.800– 3.42) | 1.10 (0.503 – 0.2.21) | |
| Pyrraline | 22.0 (12.2 – 30.4) | 24.2 (19.4 – 40.6) | |
| DT | 0.501 (0.286 – 0.771) | 0.676 (0.500 – 0.847) | |
| NFK | 15.2 (12.5 – 18.1) | 11.3 (6.23 – 14.3) | 0.030 |
| AASA | 19.7 (16.9 – 29.1) | 30.6 (21.1 – 46.4) | 0.0063 |
| GSA | 73.9 (53.2 – 129) | 109 (80.1 – 203) | 0.039 |
| 3-NT | 1.10 (0.90 – 1.26) | 1.17 (0.79 – 1.58) | |

FIGURE 6

| Amino acid | Urine (nmol/mg creatinine) | | |
|---|---|---|---|
| | Healthy controls | ASD | p-value |
| FL | 56.7 (33.8 – 128.7) | 90.8 (42.4 – 167.9) | |
| CML | 26.2 (19.7 – 34.7) | 33.1 (26.6 – 42.6) | 0.016 |
| CEL | 0.435 (0.202 – 0.848) | 0.472 (0.180 – 0.940) | |
| G-H1 | 1.88 (1.11 – 3.04) | 2.57 (1.53 – 3.75) | 0.024 |
| MG-H1 | 18.6 (8.00 – 27.4) | 24.5 (9.14 – 37.6) | |
| 3DG-H | 2.06 (0.587 – 4.38) | 2.92 (1.09 – 6.26) | |
| CMA | 1.46 (0.636 – 1.97) | 1.78 (1.14 – 2.91) | 0.037 |
| GSP | 1.58 (1.15 – 1.98) | 1.53 (1.20 – 1.98) | |
| MOLD | 0.025 (0.013 – 0.050) | 0.040 (0.017 – 0.068) | 0.027 |
| Pyrraline | 20.6 (14.9 – 44.2) | 34.2 (22.7 – 72.5) | 0.047 |
| DT | 0.070 (0.058 – 0.085) | 0.086 (0.075 – 0.109) | 0.0022* |
| NFK | 0.117 (0.084 – 0.231) | 0.179 (0.107 – 0.238) | 0.037 |
| AASA | 1.08 (0.805 – 2.76) | 1.80 (1.13 – 2.89) | 0.040 |
| GSA | 17.3 (13.2 – 22.7) | 34.5 (12.7 – 48.0) | 0.0018* |
| 3-NT | 0.0044 (0.001 – 0.010) | 0.0077 (0.003 – 0.014) | |

FIGURE 7

| Amino acid | Plasma (µM) | | p-value |
|---|---|---|---|
| | Healthy controls | ASD | |
| Ala | 294 ± 71.5 | 330 ± 98.3 | |
| Arg | 39.4 ± 10.3 | 48.4 ± 16.6 | 0.016 |
| Asn | 33.2 ± 4.57 | 34.3 ± 10.6 | |
| Asp | 35.5 ± 7.37 | 37.0 ± 10.0 | |
| Cys (total) | 41.7 ± 10.4 | 46.1 ± 15.0 | |
| Gln | 463 ± 38.6 | 496 ± 61.2 | 0.024 |
| Glu | 1672 ± 324 | 1999 ± 619 | 0.034 |
| Gly | 272 (187 – 1061) | 241 (121 – 515) | |
| His | 68.0 ± 8.51 | 72.8 ± 9.96 | |
| Ile | 50.7 ± 15.3 | 51.6 ± 12.4 | |
| Leu | 126 ±34.4 | 132 ± 25.6 | |
| Lys | 132 ± 20.3 | 146 ± 36.7 | |
| Met | 23.1 ± 6.41 | 26.2 ± 5.84 | |
| Phe | 68.9 ± 11.3 | 68.8 ± 16.8 | |
| Pro | 195 ± 65.4 | 223 ± 94.7 | |
| Ser | 128 ± 23.5 | 132 ± 18.7 | |
| Thr | 116 ± 36.0 | 141 ± 46.8 | 0.041 |
| Trp | 5.22 ± 1.26 | 3.92 ± 2.40 | 0.0055 |
| Tyr | 84.4 ± 21.3 | 87.9 ± 26.8 | |
| Val | 125 ± 31.3 | 120 ± 26.0 | |

FIGURE 8

| Amino acid | Urine (nmol/mg creatinine) | | |
|---|---|---|---|
| | Healthy controls | ASD | p-value |
| Ala | 301 (224 -432) | 392 (305 – 533) | 0.030 |
| Arg | 52.1 ± 17.1 | 64.0 ± 18.0 | 0.014 |
| Asn | 92.4 (72.1 -132) | 169 (123 -236) | 0.0012* |
| Asp | 142 (112 – 179) | 160 (117 – 241) | |
| Cys (total) | 25.3 (20.4 – 35.9) | 28.3 (21.1 – 43.3) | |
| Gln | 529 (452 – 704) | 741 (609 – 876) | 0.0048 |
| Glu | 373 (254 – 495) | 475 (367 – 690) | 0.010 |
| Gly | 1.12 (1.19 – 2.78) | 2.58 (1.84 – 3.45) | 0.019 |
| His | 2.19 ± 0.88 | 2.90 ± 1.21 | 0.027 |
| Ile | 13.0 ± 4.37 | 18.1 ±6.50 | 0.0059 |
| Leu | 43.1 ±13.6 | 52.0 ± 13.5 | 0.028 |
| Lys | 136 (83.3 – 264) | 171 (117 – 352) | |
| Met | 17.9 ± 7.98 | 23.1 ± 7.20 | 0.0037 |
| Phe | 101 ± 38.9 | 110 ± 32.9 | |
| Pro | 14.5 ± 6.21 | 20.7 ± 5.37 | 0.00073** |
| Ser | 461 (413 – 621) | 677 (519 – 910) | 0.0021* |
| Thr | 216 (170 – 265) | 283 (221 - 405) | 0.0039 |
| Trp | 114 ± 73.6 | 164 ± 48.6 | 0.0043 |
| Tyr | 204 (133 – 255) | 240 (173 – 317) | |
| Val | 25.6 ± 9.52 | 34.8 ±10.9 | 0.00073** |

FIGURE 9

| Amino acid | Renal clearance (μl/mg creatinine) | | p-value |
|---|---|---|---|
| | Healthy controls | ASD | |
| FL# | 0.696 (0.375 – 1.16) | 0.866 (0.384 – 2.31) | |
| CML | 0.297 (0.249 – 0.387) | 0.259 (0.171 – 0.782) | |
| CEL | 0.0068 (0.003 – 0.019) | 0.0042 (0.002 – 0.011) | |
| G-H1 | 21.2 (13.1 – 34.7) | 23.9 (15.0 – 57.7) | |
| MG-H1# | 0.718 (0.496 – 1.04) | 0.628 (0.363– 0.912) | |
| 3DG-H | 0.067 (0.033 – 0.163) | 0.087 (0.042 – 0.131) | |
| CMA | 1.57 (0.997 – 2.08) | 0.791 (0.465– 1.36) | 0.0011* |
| GSP | 0.121 (0.083 – 0.274) | 0.112 (0.067– 0.195) | |
| MOLD | 0.214 (0.075 – 0.487) | 0.269 (0.153 – 0.656) | |
| Pyrraline | 0.81 (0.58 – 1.17) | 1.07 (0.64 – 1.96) | |
| DT | 0.119 (0.657 – 2.02) | 0.747 (0.545 – 0.107) | 0.0025 |
| NFK | 0.062 (0.038 – 0.109) | 0.096 (0.049 – 0.139) | 0.030 |
| GSA | 29.9 (11.1– 45.8) | 17.8 (1.96 – 26.1) | |
| 3-NT | 0.068 (0.034 – 0.100) | 0.042 (0.036 – 0.129) | |

FIGURE 10

| Amino acid | Renal clearance (ml/mg creatinine) | | p-value |
|---|---|---|---|
| | Healthy controls | ASD | |
| Ala | 1.03 (0.746 – 1.712) | 1.27 (0.890 – 1.65) | |
| Arg | 0.011 (0.009 – 0.015) | 0.008 (0.006 – 0.010) | 0.0019* |
| Asn | 2.80 (2.22 – 4.76) | 4.30 (3.05 – 7.14) | 0.0055 |
| Asp | 3.81 (3.04 – 4.96) | 4.73 (2.92 – 7.82) | |
| Cys (total) | 0.646 (0.518 – 0.812) | 0.629 (0.452 – 1.133) | |
| Gln | 1.18 (0.913 – 1.53) | 1.54 (1.14 – 1.96) | 0.025 |
| Glu | 0.210 (0.158 – 0.304) | 0.243 (0.179 – 0.357) | 0.049 |
| Gly | 0.0050 (0.002 – 0.009) | 0.0067 (0.004 – 0.029) | 0.018 |
| His | 0.029 (0.024 – 0.040) | 0.040 (0.027 – 0.053) | |
| Ile | 0.262 (0.192 – 0.347) | 0.354 (0.256 - 0.441) | 0.0116 |
| Leu | 0.358 ± 0.135 | 0.402 ± 0.105 | |
| Lys | 0.011 (0.005 – 0.018) | 0.0071 (0.005 – 0.011) | |
| Met | 0.0066 ± 0.0015 | 0.0056 ± 0.0023 | |
| Phe | 1.32 (0.959 – 2.02) | 1.65 (1.33– 1.95) | |
| Pro | 0.077 ± 0.031 | 0.104 ± 0.039 | 0.0138 |
| Ser | 3.66 (2.95 – 4.79) | 5.22 (3.99 – 6.78) | 0.0081 |
| Thr | 2.023 ± 0.765 | 2.44 ± 1.05 | |
| Trp | 0.209 (0.155 – 0.242) | 0.287 (0.166 – 0.497) | 0.010 |
| Tyr | 0.0209 (0.016 – 0.025) | 0.015 (0.012 – 0.025) | |
| Val | 0.0017 (0.0014 – 0.0022) | 0.0016 (0.0013 – 0.0026) | |

FIGURE 11A
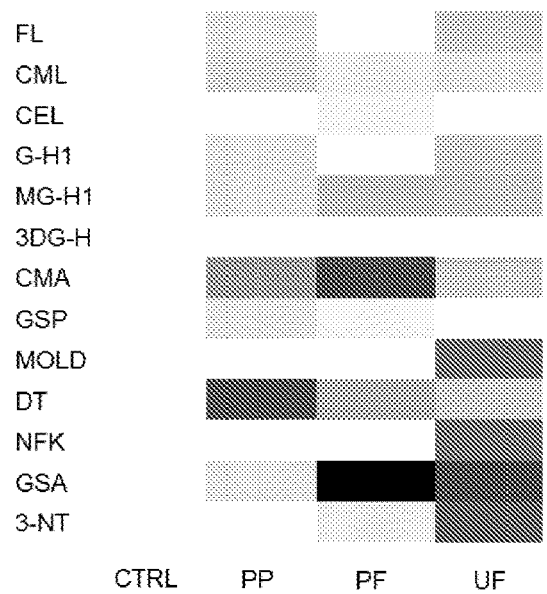
FIGURE 11B
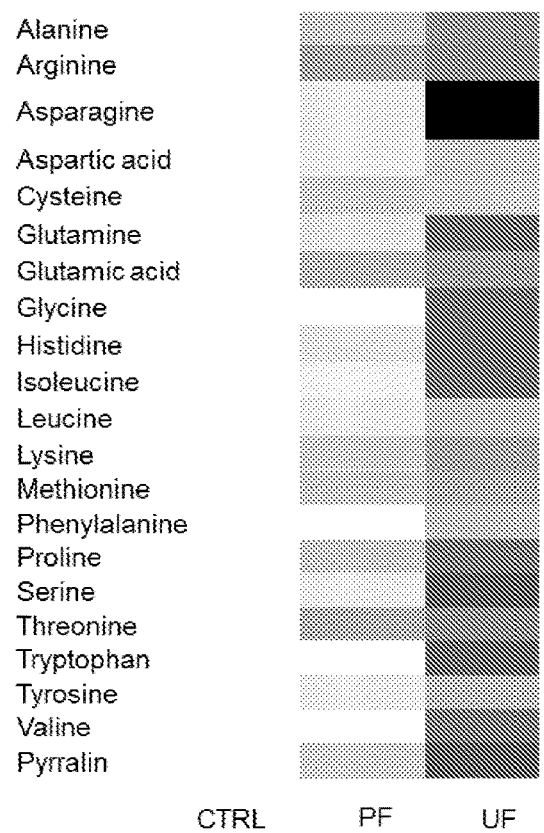

FIGURE 14

| Algorithm no | 1 | 2 | 3 | 4 |
|---|---|---|---|---|
| Compartment and analyte | Plasma protein adduct residues | Plasma amino acids | Plasma protein adduct residues and amino acids | Urinary amino acids |
| Features | CML, 3DG-H, CMA & DT | CML & CMA | CML, 3DG-H, CMA & DT residues with G-H1 & GSA free adducts | GSA & Pyrraline free adducts |
| Accuracy (%) | 88.3 (85.5 – 91.2) | 74.8 (71.7 – 77.9) | 89.0 (87.0 – 91.0) | 76.8 (74.6 – 79.0) |
| Sensitivity (%) | 91.9 (89.1 – 94.6) | 80.5 (75.1 – 86.0) | 90.4 (87.7 – 93.1) | 77.1 (73.4 – 80.8) |
| Specificity (%) | 83.9 (79.3 – 88.4) | 67.1 (58.9 – 75.4) | 87.3 (84.1 – 90.5) | 76.4 (72.0 – 80.8) |
| AUROC | 0.94 (0.91 – 0.96) | 0.80 (0.77 – 0.83) | 0.95 (0.94 – 0.96) | 0.79 (0.76 – 0.81) |
| Positive likelihood ratio | 5.69 (4.49 – 6.89) | 2.85 (2.16 – 3.55) | 7.23 (6.09 – 8.38) | 4.16 (2.88 – 5.44) |
| Negative likelihood ratio | 0.10 (0.07 – 0.13) | 0.28 (0.21 – 0.35) | 0.11 (0.08 – 0.14) | 0.30 (0.25 – 0.34) |
| Positive predictive value (%) | 88.2 (85.0 – 91.4) | 77.1 (72.9 – 81.4) | 90.2 (87.9 – 92.5) | 80.6 (77.6 – 83.5) |
| Negative predictive value (%) | 89.1 (85.5 – 92.6) | 75.0 (70.6 – 79.4) | 88.0 (85.1 – 91.0) | 73.7 (71.0 – 76.5) |
| F-score | 0.90 (0.87 – 0.92) | 0.78 (0.75 – 0.81) | 0.90 (0.88 – 0.92) | 0.78 (0.76 – 0.81) |

FIGURE 15
A
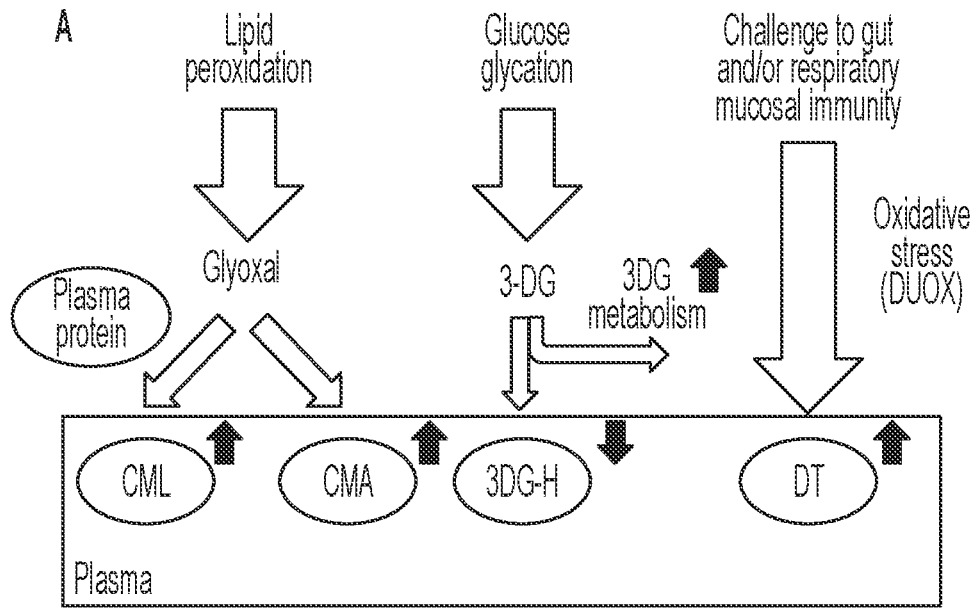
B
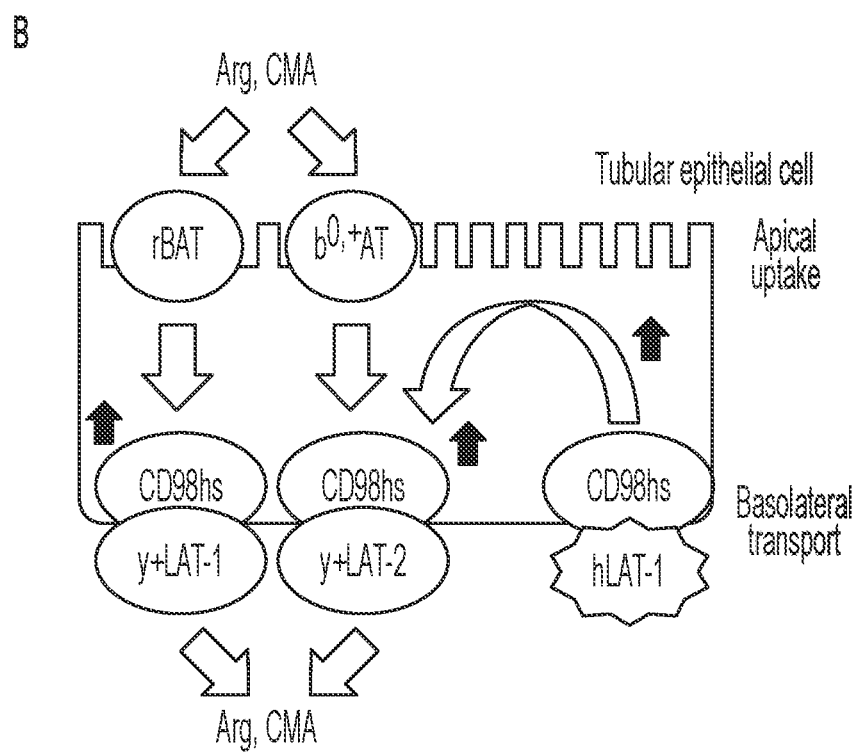

FIGURE 16

| Analyte group | Analyte | Rt (min) | Parent ion (Da) | Fragment ion (Da) | CE (eV) | Neutral fragment loss(es) | Internal standard and amount added |
|---|---|---|---|---|---|---|---|
| Glycation | FL | 28.5 | 291.0 | 84.3 | 31 | $H_2CO_2$, fructosylamine | [$^2H_4$]FL, 0.3 pmol |
| | CML | 28.5 | 204.9 | 130.1 | 12 | $NH_2CH_2CO_2H$ | [$^{13}C_6$]CML, 0.25 pmol |
| | CEL | 28.8 | 219.2 | 130.1 | 13 | $NH_2CH(CH_3)CO_2H$ | [$^{13}C_6$]CEL, 0.25 pmol |
| | G-H1 | 12.4 | 215.0 | 100.2 | 14 | $NH_2CH(CO_2H)CH_2CH=CH_2$ | [$^{15}N_2$]G-H1, 0.25 pmol |
| | MG-H1† | 11.6 & 12.5 | 229.2 | 114.3 | 14 | $NH_2CH(CO_2H)CH_2CH=CH_2$ | [$^{15}N_2$]MG-H1, 1.25 pmol |
| | 3DG-H | 11.2, 12.6 & 13.5 | 319.1 | 114.8 | 20 | $NH_2CH(CO_2H)CH_2CH=CH_2$ | [$^{15}N_2$]3DG-H, 0.25 pmol |
| | CMA | 12.1 | 233.0 | 70.1 | 27 | $H_2CO_2$, $NH_2C(=NH)NHCH_2CO_2H$ | [$^{13}C_2$]CMA, 0.25 pmol |
| | MOLD | 14.0 | 341.2 | 212.3 | 21 | $NH_2CH(CO_2H)CH_2CH_2CH=CH_2$ | [$^2H_8$]MOLD, 0.10 pmol |
| | GSP | 16.5 | 429.2 | 382.1 | 35 | $C_2H_5O$ | [$^{13}C_6$]Glucosepane, 0.25 pmol |
| | Pyrraline | 17.9 | 255.2 | 84.3 | 23 | 2-CHO-5-HOCH$_2$-pyrrole, $H_2CO_2$ | [$^{13}C_6$, $^{15}N_2$]Pyrraline, 1.00 pmol |

FIGURE 16 (continued)

| Analyte group | Analyte | Rt (min) | Parent ion (Da) | Fragment ion (Da) | CE (eV) | Neutral fragment loss(es) | Internal standard and amount added |
|---|---|---|---|---|---|---|---|
| Oxidative | MetSO | 8.7 | 166.1 | 102.2 | 14 | $CH_3$-SOH | [$^2H_3$]MetSO, 0.25 pmol |
| | DT | 19.9 | 361.2 | 315.3 | 15 | $H_2CO_2$ | [$^2H_3$]DT, 0.25 pmol |
| | NFK | 21.5 | 235.8 | 191.2 | 18 | $H_2CO_2$ | [$^{15}N_2$]NFK, 0.25 pmol |
| | AASA | 10.7 | 128.0 | 82.0 | 15 | $H_2CO_2$ | [$^2H_3$]AAA (Rt = 29.4), 2.5 pmol |
| | GSA | 32.2 | 114.0 | 68.0 | 15 | $H_2CO_2$ | [$^2H_3$]AAA (Rt = 29.4), 2.5 pmol |
| Nitration | 3-NT | 23.2 | 227.1 | 181.2 | 13 | $H_2CO_2$ | [$^2H_3$]3-NT, 0.25 pmol |
| Amino acids | Ala | 5.2 | 90.1 | 44.1 | 8 | $H_2CO_2$ | [$^2H_3$]Ala, 250 pmol |
| | Arg | 29.2 | 175.2 | 70.3 | 15 | $H_2CO_2$, $NH_2C(=NH)NH_2$ | [$^{15}N_2$]Arg, 250 pmol |
| | Asn | 7.2 | 133.2 | 74.1 | 14 | $CH_3CONH_2$ | [$^{13}C_4$]Asp, 250 pmol |
| | Asp | 7.5 | 134.1 | 88.0 | 10 | $H_2CO_2$ | [$^{13}C_2$,$^{15}N_1$]Asp, 250 pmol |

FIGURE 16 (continued)

| Analyte group | Analyte Rt (min) | Parent ion (Da) | Fragment ion (Da) | CE (eV) | Neutral fragment loss(es) | Internal standard and amount added |
|---|---|---|---|---|---|---|
| Cys | 6.6 | 122.0 | 59.0 | 18 | $H_2CO_2 + NH_3$ | [$^{13}C_3$,$^{15}N_1$]Cys, 250 pmol |
| Cystine$_2$ | 32.6 | 241.1 | 120.1 | 20 | $C_3H_7NO_2S$ (cys) | [$^2H_4$]Cys, 250 pmol |
| Gln | 9.9 | 147.2 | 84.1 | 10 | $H_2CO_2 + NH_3$ | [$^{13}C_5$]Gln, 250 pmol |
| Glu | 28.4 | 148.1 | 102.1 | 10 | $H_2CO_2$ | [$^{13}C_5$]Glu, 250 pmol |
| Gly | 4.8 | 76.2 | 30.1 | 6 | $H_2CO_2$ | [$^{13}C_2$,$^{15}N_1$]Gly, 250 pmol |
| His | 32.6 | 156.1 | 93.0 | 22 | $H_2CO_2 + NH_3$ | [$^{13}C_6$]His, 250 pmol |
| Ile | 31.5 | 132.3 | 86.2 | 10 | $H_2CO_2$ | [$^{13}C_6$]Ile, 250 pmol |
| Leu | 27.6 | 132.3 | 86.2 | 10 | $H_2CO_2$ | [$^2H_3$]Leu, 250 pmol |
| Lys | 5.5 | 147.1 | 84.3 | 15 | $H_2CO_2$, $NH_3$ | [$^{13}C_6$]Lys, 250 pmol |
| Met | 20.5 | 150.0 | 104.2 | 11 | $H_2CO_2$ | [$^2H_3$]Met, 250 pmol |

FIGURE 16 (continued)

| Analyte group | Analyte | Rt (min) | Parent ion (Da) | Fragment ion (Da) | CE (eV) | Neutral fragment loss(es) | Internal standard and amount added |
|---|---|---|---|---|---|---|---|
| | Orn | 5.2 | 133.1 | 70.1 | 9 | $H_2CO_2$, $NH_3$ | [$^2H_6$]Orn, 50 pmol |
| | Phe | 17.2 | 166.1 | 103.1 | 26 | $H_2CO_2$, $NH_3$ | [ring-$^2H_5$]Phe, 250 pmol |
| | Pro | 6.6 | 116.1 | 70.1 | 12 | $H_2CO_2$ | [$^{13}C_5$]Pro, 250 pmol |
| | Ser | 5.2 | 106.0 | 42.0 | 18 | $H_2CO_2$, $H_2O$ | [$^{13}C_3$]Ser, 250 pmol |
| | Thr | 5.9 | 120.1 | 56.1 | 14 | $H_2CO_2$, $H_2O$ | [$^{13}C_4$]Thr, 250 pmol |
| | Trp | 23.5 | 205.0 | 159.1 | 15 | $H_2CO_2$ | [$^{15}N_2$]Trp, 250 pmol |
| | Tyr | 18.3 | 182.1 | 136.2 | 13 | $H_2CO_2$ | [$^2H_4$]Tyr, 250 pmol |
| | Val | 8.2 | 117.8 | 72.0 | 19 | $H_2CO_2$ | [$^2H_8$]Val, 250 pmol |

FIGURE 22

| Algorithm no | 1 | | 2 | | 3 | | 4 | |
|---|---|---|---|---|---|---|---|---|
| nCorrect | 12/14 | | 10/14 | | 14/14 | | 15/19 | |
| | Predicted class | | Predicted class | | Predicted class | | Predicted class | |
| | ASD | Control | ASD | Control | ASD | Control | ASD | Control |
| Clinical class ASD | 12 | 2 | 10 | 4 | 14 | 0 | 15 | 4 |
| Control | 0 | 10 | 2 | 8 | 2 | 8 | 1 | 15 |

METHODS FOR DIAGNOSING AN AUTISTIC SPECTRUM DISORDER

This application is the U.S. national stage entry of the PCT Application No. PCT/GB2019/050362, filed on Feb. 11, 2019, which claims priority to GB Patent Application No. 1802116.2, filed on Feb. 9, 2018, the disclosures of the foregoing applications are incorporated herein by reference in their entirety.

The present invention relates to methods for diagnosing an autistic spectrum disorder (ASD) comprising the use of an amino acid adduct.

Autism Spectrum Disorders (ASD) are defined as developmental disorders mainly affecting social interactions and range of interests and causing a wide spectrum of other disabilities, such as speech disturbances, repetitive and/or compulsive behaviours, hyperactivity, anxiety and difficulty to adapt to new environments, with or without cognitive impairment. The high heterogeneity of the clinical presentation makes diagnosis of ASD difficult and uncertain, particularly at the early stages of development. Autism affects about 1% of children and typically has higher prevalence in boys (1.5%) than girls (0.5%).

ASD is currently diagnosed on the basis of a clinician's perception of symptoms in the patient. Scores derived from assessment of patient performance in standardized activities are used, including Autism Diagnostic Observation Schedule (ADOS) score, the childhood autism rating scale (CARS), checklist for autism in toddlers (CHAT) and social communication questionnaire (SCQ). However, these assessments are subjective and provide no information on assessment of risk of progression to more severe symptoms nor assessment of response to therapy. The performance of these methods is poor, they have a sensitivity of only 20-70% and 50-80%. They also require expert an experienced healthcare personnel for implementation. There therefore exists a need for improved methods of diagnosing autism in patients.

Currently, there is no clinical chemistry or imaging test for autism. Diagnosis is based on clinical assessment of impaired social interactions and range of interests—as described above. Transcriptomic, proteomic and metabolomic profiling have been proposed for diagnosis of ASD, with diagnostic performance judged by area under-the-curve of receiver operating characteristic (AUROC) plot of 0.73-0.91. However, such prior art methods are of low specificity. Despite these recent developments, there remains a need for an inexpensive and minimally invasive test for diagnosing a subject with ASD with a high degree of sensitivity and specificity.

The present invention solves at least one of the above-mentioned problems, by providing a diagnostic method based on detecting trace levels of chemically-defined oxidised, nitrated and glycated amino acid residues in plasma protein and related oxidised, nitrated and glycated amino acids in plasma and urine (e.g. in children with normal development and age and gender matched children with ASD). Furthermore, machine learning steps (a data-driven selection of optimum combinations of these metabolites in algorithms) to distinguish between children with and without ASD are provided.

The present inventors have found that quantifying concentrations of protein glycation, oxidation and nitration adducts in plasma protein and related free adducts in plasma and urine of children with ASD and healthy controls has robust diagnostic utility for ASD.

Advantageously, the diagnosis of ASD may now be made by the measurement of a blood or urine sample. The present method of diagnosis is objective and has high sensitivity and/or specificity and/or accuracy. It may be performed by non-experts with routine clinical chemistry training in a short time period (e.g. 30 minutes). This test is suitable for screening children (e.g. children suspected of having ASD, or being predisposed to having ASD).

Thus, the invention provides in one aspect a method for diagnosing an autistic spectrum disorder (ASD), said method comprising:
  a. detecting the concentration of an amino acid adduct in a sample obtained from a subject, wherein said amino acid adduct is a glycated amino acid adduct, an oxidised amino acid adduct, or a nitrated amino acid adduct;
  b. comparing the concentration of the amino acid adduct in the sample with the concentration of the same amino acid adduct in a reference standard; and
  c. identifying the presence or absence of a concentration difference of said amino acid adduct in the sample relative to the reference standard;
     wherein the presence or absence of a concentration difference correlates with the presence or absence of ASD.

Advantageously, changes in the concentration of said amino acid adducts correlates with the presence or absence of ASD.

Detecting the presence or absence of ASD may further allow the determination of a good or poor prognosis. The presence of ASD allows a determination of a poor prognosis, while the absence of ASD allows the determination of a good prognosis. Thus, in one aspect the invention also provides a method for determining prognosis of an autistic spectrum disorder (ASD), said method comprising:
  a. detecting the concentration of an amino acid adduct in a sample obtained from a subject, wherein said amino acid adduct is a glycated amino acid adduct, an oxidised amino acid adduct, or a nitrated amino acid adduct;
  b. comparing the concentration of the amino acid adduct in the sample with the concentration of the same amino acid adduct in a reference standard; and
  c. identifying the presence or absence of a concentration difference of said amino acid adduct in the sample relative to the reference standard;
     wherein the presence or absence of a concentration difference correlates with a good prognosis or a poor prognosis.

The term "Autistic Spectrum Disorder" or "Autism Spectrum Disorder" ("ASD") as used herein encompasses a diverse group of developmental disorders typically affecting social interactions and range of interests and causing a wide spectrum of other disabilities, such as speech disturbances, repetitive and/or compulsive behaviours, hyperactivity, anxiety and difficulty to adapt to new environments, with or without cognitive impairment. Such disorders may include autism, Asperger syndrome, pervasive developmental disorder not otherwise specified (PDD-NOS) and childhood disintegrative disorder. Preferably the term ASD means autism.

The terms "subject", "individual" and "patient" are used interchangeably herein to refer to a mammalian subject. In one embodiment the "subject" is a human, a companion animal (e.g. a pet such as dogs, cats, and rabbits), livestock (e.g. pigs, sheep, cattle, and goats), and horses. In a preferable embodiment, the subject is a human, such as a human child. In methods of the invention, the subject may not have been previously diagnosed as having ASD. Alternatively, the subject may have been previously diagnosed as having ASD. The subject may also be one who exhibits disease risk factors, or one who is asymptomatic for ASD. The subject may also be one who is suffering from or is at risk of developing ASD. In one embodiment, the subject is a typically developing subject. The skilled person understands that a typically developing subject is a subject at high risk of having or developing ASD. Thus, in one embodiment, a method of the invention may be used to confirm the presence of ASD in a subject. For example, the subject may previously have been diagnosed with ASD through analysis of symptoms that the subject presents.

A detecting step (e.g. of an amino acid adduct) may be performed using any suitable method known in the art. For example mass spectrometry may be used. In one embodiment a detecting step is performed using liquid chromatography-tandem mass spectrometry, such as stable isotopic dilution analysis liquid chromatography-tandem mass spectrometry (LC-MS/MS). In another embodiment, the detecting step is performed by way of an immunoassay. Said immunoassay may employ the use of one or more antibodies that bind to one or more of the amino acid adducts described herein. Thus, in one aspect, there is provide an antibody composition for use in the diagnosis of an autistic spectrum disorder in a subject, wherein said antibody composition binds one or more amino acid adduct described herein. A method of the invention may comprise the use of a kit of the invention or a part thereof. For example, the method may comprise the use of a reagent described herein (preferably an isotopic reagent) and preferably comprises the use of a standard (e.g. an isotopic standard) described herein.

Detecting the concentration of an amino acid adduct in a sample preferably involves quantifying the amino acid adduct by determining, for example, the relative or absolute amount thereof. It will be appreciated that the assay methods do not necessarily require measurement of absolute concentrations of an amino acid adduct, unless it is desired, because relative values may be sufficient for many applications of the invention. Accordingly, the "concentration" can be the (absolute) total concentration of the amino acid adduct that is detected in a sample, or it can be a "relative" concentration, e.g., the difference between the amino acid adduct detected in a sample and e.g. another constituent of the sample. In some embodiments, the concentration of the amino acid adduct may be expressed by its concentration in a sample, or by the concentration of a reagent that detects the amino acid adduct. In one embodiment, a method of the invention may further involve detecting the concentration of creatinine in the sample. As such, when detecting the concentration of an amino acid adduct in a method of the invention, the concentration of the amino acid adduct may be normalised to the concentration of creatinine detected in the sample.

The methods or uses of the invention may encompass the detection of a concentration increase or decrease. The methods or uses of the invention may also encompass detecting no change (or substantially no change) in concentration.

The increase may be an increase of at least 5%, 10%, 15%, 20%, 25%, 30%, 35%, 40%, 45%, 50%, 60%, 70%, 80%, 90%, 100%, 110%, 120%, 130%, 140% or 150% in the concentration of an amino acid adduct when compared to the reference standard. Said amino acid adduct concentration increase is preferably statistically significant. In some embodiments, said increase may be identified by a fold change of concentration (e.g. expressed in $\log_2$). In one embodiment a concentration increase may be at least about 1.1-fold, 1.2-fold, 1.25-fold or 1.5-fold greater when compared to a reference standard.

The decrease may be at least 5%, 10%, 15%, 20%, 25%, 30%, 35%, 40%, 45%, 50%, 60%, 70%, 80%, 90%, 95%, or 99% in the concentration of an amino acid adduct when compared to the reference standard. Said amino acid adduct concentration difference is preferably statistically significant. In some embodiments, said decrease may be identified by a fold change of concentration (e.g. expressed in $\log_2$). In one embodiment a concentration decrease may be at least about −1.1-fold, −1.2-fold, −1.25-fold or −1.5-fold when compared to a reference standard.

A method of the invention preferably involves the use of a diagnostic algorithm or other data-driven combinatorial approach. In one embodiment the detected concentrations of amino acid adducts are entered into a diagnostic algorithm (e.g. as part of a computer software programme which may in one aspect be provided by the present invention), and said diagnostic algorithm indicates whether ASD is present or absent. In one aspect there is provided software adapted to provide a diagnostic algorithm or diagnostic method of the invention. The invention also extends to a processor adapted to provide said software, diagnostic algorithm and/or diagnostic method.

The skilled person will appreciate that any suitable algorithm can be used (including any of the algorithms described herein). In one embodiment the diagnostic algorithm is one or more selected from: Random Forests, logistic regression, ensemble classifier, Support Vector Machines (SVMs), general linear models (GLM), and GLMNET. Preferably the algorithm is SVMs.

In one embodiment, steps (b) and/or (c) are conducted using a diagnostic algorithm configured to diagnose the presence or absence of ASD based on the concentration of the amino acid adduct detected in the sample, wherein the diagnostic algorithm is trained on the corresponding concentration for the same amino acid adduct in one or more (preferably a plurality of) reference standards. The reference standards may preferably be ASD and non-ASD reference standards. In some embodiments the algorithm provides different predictive weightings to different amino acid adducts to improve specificity and/or sensitivity and/or accuracy of the diagnostic method. Said embodiment can be applied to the other methods such as the methods for determining prognosis.

Thus there is provided in one aspect a method for diagnosing an autistic spectrum disorder (ASD), said method comprising:

a. detecting the concentration of an amino acid adduct in a sample obtained from a subject, wherein said amino acid adduct is a glycated amino acid adduct, an oxidised amino acid adduct, or a nitrated amino acid adduct; and b. using a diagnostic algorithm to diagnose the presence or absence of ASD based on the concentration of the amino acid adduct detected in the sample, wherein the diagnostic algorithm is trained on the corresponding concentration for the same amino acid adduct in one or more (preferably a plurality of) reference standards.

Similar methods for determining prognosis, identifying a therapy suitable for treating ASD, and monitoring the efficacy of an ASD therapy are also provided.

In embodiments related to methods for identifying an ASD therapy, detecting the absence of ASD may be indicative of a candidate therapy that is suitable for treating ASD, whereas detecting the presence of ASD may be indicative of a candidate therapy that is not suitable for treating ASD.

In embodiments related to methods for monitoring efficacy of an ASD therapy, detecting the absence of ASD may be indicative of the presence efficacy, whereas detecting the presence of ASD may be indicative of the absence of efficacy.

In one embodiment, steps (b) and/or (c) are conducted with/using a diagnostic algorithm configured to classify the health of the subject based on the concentration of the amino acid adduct detected in the sample with said diagnostic algorithm, wherein the diagnostic algorithm is trained on the corresponding concentration for the same amino acid adduct obtained from a population of subjects having known disease status (i.e. a reference standard). In some embodiments the algorithm provides different predictive weightings to different amino acid adducts to improve specificity and/or sensitivity and/or accuracy of the present invention.

A sample for use in the present invention is any sample that could contain an amino acid adduct. Suitably, the sample may be isolated from a subject suspected of having ASD. In some embodiments, the sample is isolated from a subject diagnosed as having ASD. Suitably, a sample may be selected from one or more of blood, urine, eye fluid, lymphatic fluid, saliva, synovial fluid, seminal fluid, cerebrospinal fluid, sebaceous secretions, and/or sputum. As will be appreciated by those skilled in the art, said sample may be pre-treated for analysis by conventional techniques as described herein and known by those skilled in the art. For example, a sample may be hydrolysed prior to detection. In one embodiment, the hydrolysis is performed enzymatically. Protein hydrolysis by enzymatic digestion is advantageous because it avoids the severe conditions of acid hydrolysis which may compromise the analyte content of the sample during pre-analytic processing. In one embodiment, enzymatic digestion may involve treatment with pepsin, optionally followed by treatment with pronase E, prolidase and aminopeptidase. Additionally, collagenase may be used, particularly, but not exclusively, where the protein to be assayed is present in the extracellular matrix. Automated exhaustive enzymatic hydrolysis may be used, thereby avoiding harsh, pre-analytic processing. In one embodiment, prior to hydrolysis, the proteins may be first washed by ultrafiltration to remove free amino acids, and retained protein is collected for hydrolysis. In one embodiment, the retained protein may be delipidated prior to hydrolysis.

Preferably the sample is a blood sample. The term "blood sample" encompasses a whole blood as well as a sample obtained after subjecting blood to one or more processing steps (such as fractionation to yield a blood fraction). For example, the blood may be a blood plasma or blood serum sample. Said sample may be a blood sample containing proteins (and optionally excluding amino acids) (e.g. a blood serum protein sample) or may be a blood sample (e.g. a filtrate such as an ultrafiltrate) where proteins have been removed. In one embodiment, the sample is a blood plasma sample, preferably wherein the blood plasma sample comprises amino acid adducts comprised in a polypeptide sequence and lacks free amino acid adducts.

A key advantage to using blood, blood plasma, blood serum and/or urine in the methods of the invention is that these samples are readily available and can be obtained using minimally invasive techniques. This is particularly advantageous when attempting to diagnose ASD in sensitive subjects (e.g. children).

In one embodiment a sample may be processed to isolate a free amino acid adduct from a sample by ultrafiltration prior to detecting the concentration of said amino acid adduct in a sample. The ultrafiltrate sample (containing a free amino acid adduct) may be collected and used in accordance with the present invention.

In one embodiment, the oxidised, nitrated and glycated free adducts are collected by microspin ultrafiltration. A molecular weight cut-off of at least about 10 kDa may be used in the ultrafiltration step. In one embodiment, the molecular weight cut-off may be at least about 5 kDa (such as at least about 6 kDa, 7 kDa, 8 kDa, 9 kDa, 10 kDa, 11 kDa, 12 kDa, 13 kDa, 14 kDa or 15 kDa). The ultrafiltration step may be performed at a temperature of between about 2° C. and 10° C., such as at about 4° C.

Thus, the term "plasma ultrafiltrate" as used herein refers to a sample obtained by subjecting blood plasma to ultrafiltration (e.g. as described above) to isolate a free amino acid adduct. Similarly, the term "urine ultrafiltrate" as used herein refers to a sample obtained by subjecting urine to ultrafiltration to isolate a free amino acid adduct.

As used herein, the term "amino acid adduct" refers to an amino acid that has been oxidised, nitrated, or glycated. The amino acid adduct may be comprised in a polypeptide sequence (e.g. an "adduct residue"). Alternatively, the amino acid adduct may be a "free adduct" (e.g. not comprised in a polypeptide sequence). In some embodiments a "free adduct" may be a proteolytic digestion product released into body fluid (e.g. blood and/or urine) of a subject following proteolysis of a polypeptide sequence comprising the amino acid adduct. In some embodiments the concentration of free adducts is detected. Alternatively or additionally, the concentration of amino acid adducts present in a polypeptide sequence are detected.

The present invention encompasses detecting an amino acid adduct or any isomer (e.g. structural isomer) thereof. For example, 3DG-H exists as 3 structural isomers and in one embodiment all 3 structural isomers are detected. MG-H1 and G-H1 also exist as 3 structural isomers. In one embodiment all 3 structural isomers of MG-H1 and G-H1 are detected, preferably isomer 1 of MG-H1 and G-H1 is detected.

Impairment of protein homeostasis leading to proteotoxic stress and activation of the unfolded protein response (UPR) has been found to be related to the presence of ASD. Drivers of impaired protein quality are increased spontaneous modifications by glycation, oxidation and nitration. Glycation of proteins occurs by spontaneous reaction of proteins with glucose, reactive dicarbonyl metabolites, glyoxal, methylglyoxal (MG) and 3-deoxyglucosone (3-DG), and other saccharides and saccharide derivatives. Protein glycation adducts are classified as: early stage glycation adducts, such as $N_\varepsilon$-fructosyl-lysine (FL) residues formed by glycation of proteins by glucose; and late-stage adducts known as advanced glycation endproducts (AGEs), such as $N_\varepsilon$-carboxymethyl-lysine (CML) and glucosepane (GSP) residues formed by the degradation of FL residues, glyoxal-derived hydroimidazolone (G-H1), methylglyoxal-derived hydroimidazolone (MG-H1) and 3-deoxyglucosone-derived hydroimidazolone (3DG-H) (formed by the modification of arginine residues by glyoxal MG and 3-DG, respectively), $N_\omega$-carboxymethylarginine (CMA) (also formed by the reaction of glyoxal with arginine residues), and methylglyoxal-derived lysine crosslink (MOLD). Protein oxidation occurs by the reaction of proteins with reactive oxygen species (ROS) and is increased in oxidative stress. Examples of protein oxidation adducts are: dityrosine (DT), N-formylkynurenine (NFK), α-aminoadipic semialdehyde (AASA) and glutamic semialdehyde (GSA) residues. Increased oxidative damage associated with oxidative stress and neuroinflammation may be common features of ASD (e.g. in children). Protein nitration occurs by the reaction of proteins with reactive nitrogen species such as peroxynitrite. The main adduct formed by protein nitration is 3-nitrotyrosine (3-NT) residues (FIG. 1B). Increased protein damage by these mechanisms may lead to activation of the UPR to counter the proteotoxic threat and related inflammatory response. Glycated, oxidized and nitrated proteins undergo proteolysis to form related glycated, oxidized and nitrated amino acids—also called glycation, oxidation and nitration free adducts. Glycated, oxidized and nitrated amino acids are released into plasma and are excreted in urine. Urinary excretion of glycation, oxidation and nitration free adducts are approximate measures of whole body fluxes of protein glycation, oxidation and nitration, respectively. There are also minor contributions to the pool of these metabolites by direct glycation, oxidation and nitration of amino acids and absorption from food after digestion of damaged proteins therein.

In one embodiment an amino acid adduct is a glycated amino acid adduct.

A glycated amino acid adduct may be one or more selected from $N_\varepsilon$-fructosyl-lysine (FL), glyoxal-derived hydroimidazolone (G-H1), $N_\varepsilon$-(1-carboxyethyl)lysine (CEL), 3-deoxyglucosone-derived hydroimidazolone (3DG-H), $N_\varepsilon$-carboxymethyl-lysine (CML), $N_\omega$-carboxymethyl-arginine (CMA), methylglyoxal-derived hydroimidazolone (MG-H1), pyrraline, glucosepane (GSP) and methylglyoxal-derived lysine dimer (MOLD).

In one embodiment an amino acid adduct is an oxidised amino acid adduct.

An oxidised amino acid adduct may be one or more selected from dityrosine (DT), N-formylkynurenine (NFK), α-aminoadipic semialdehyde (AASA) and glutamic semialdehyde (GSA) (preferably one or more selected from NFK, AASA and GSA).

In one embodiment an amino acid adduct is a nitrated amino acid adduct. A nitrated amino acid adduct may be 3-Nitrotyrosine (3-NT).

In some embodiments the invention comprises detecting the concentration of a glycated amino acid, an oxidised amino acid, and/or a nitrated amino acid. Preferably the invention comprises detecting the concentration of a glycated amino acid and an oxidised amino acid. In some embodiments the concentration of a conventional (standard) amino acid may also be detected (e.g. as described in the section "Conventional Amino Acids" herein). Said conventional amino acids may be one or more selected from: alanine, cysteine, aspartate, glutamate, phenylalanine, glycine, histidine, isoleucine, lysine, leucine, methionine, asparagine, pyrrolysine, proline, glutamine, arginine, serine, threonine, selenocysteine, valine, tryptophan, and tyrosine.

Preferably the amino acid adduct is one or more selected from Nε-carboxymethyl-lysine (CML), 3-deoxyglucosone-derived hydroimidazolone (3DG-H), Nω-carboxymethyl-arginine (CMA), dityrosine (DT), glutamic semialdehyde (GSA), glyoxal-derived hydroimidazolone (G-H1), pyrraline, methylglyoxal-derived hydroimidazolone (MG-H1), $N_\varepsilon$-fructosyl-lysine (FL), $N_\varepsilon$-(1-carboxyethyl)lysine (CEL), α-aminoadipic semialdehyde (AASA), and methylglyoxal-derived lysine dimer (MOLD) (more preferably one or more selected from CML, 3DG-H, CMA, GSA, G-H1, pyrraline, MG-H1, FL, CEL, AASA and MOLD).

More preferably an amino acid adduct is one or more selected from Nε-carboxymethyl-lysine (CML), 3-deoxyglucosone-derived hydroimidazolone (3DG-H), Nω-carboxymethylarginine (CMA), dityrosine (DT), glutamic semialdehyde (GSA), glyoxal-derived hydroimidazolone (G-H1), and pyrraline (and even more preferably one or more selected from CML, 3DG-H, GSA, G-H1, and pyrraline).

In one embodiment:
a. the concentration of one or more (preferably all) selected from: CML, CMA, DT, and GSA (preferably CML, CMA, and/or GSA) is increased; and/or (preferably and)
b. the concentration of one or more (preferably all) selected from: 3DG-H and G-H1 (free adduct) is decreased;
when compared to a non-ASD reference standard, and preferably indicates the presence of ASD (e.g. said concentration profile is correlated to the presence of ASD). The skilled person will appreciate that where the amino acid adduct concentration profiles detailed above are not detected, that this preferably indicates the absence of ASD. Preferably the sample is a blood sample.

In another embodiment:
a. the concentration of one or more (preferably all) selected from: CML, CMA, DT, and GSA (preferably CML, CMA and/or GSA) is the same or increased; and/or (preferably and)
b. the concentration of one or more (preferably all) selected from: 3DG-H and G-H1 (free adduct) is the same or decreased;
when compared to an ASD reference standard, and preferably indicates the presence of ASD (e.g. said concentration profile is correlated to the presence of ASD). The skilled person will appreciate that where the amino acid adduct concentration profiles detailed above are not detected, that this preferably indicates the absence of ASD. Preferably the sample is a blood sample.

In one embodiment:
a. the concentration of one or more (preferably all) selected from: CML, CMA, and DT (preferably CML and/or CMA) is increased; and/or (preferably and)
b. the concentration of 3DG-H is decreased;
when compared to a non-ASD reference standard, and preferably indicates the presence of ASD (e.g. said concentration profile is correlated to the presence of ASD). The skilled person will appreciate that where the amino acid adduct concentration profiles detailed above are not detected, that this preferably indicates the absence of ASD. Preferably the sample is a blood plasma protein sample.

In one embodiment:
a. the concentration of one or more (preferably all) selected from: CML, CMA, and DT (preferably CML and/or CMA) is the same or increased; and/or (preferably and)
b. the concentration of 3DG-H is the same or decreased;
when compared to an ASD reference standard, and preferably indicates the presence of ASD (e.g. said concentration profile is correlated to the presence of ASD). The skilled person will appreciate that where the amino acid adduct concentration profiles detailed above are not detected, that this preferably indicates the absence of ASD. Preferably the sample is a blood plasma protein sample.

In one embodiment the concentration of CML and/or CMA (preferably CML and CMA) is increased when compared to a non-ASD reference standard. Preferably the sample is a blood plasma ultrafiltrate sample.

In one embodiment the concentration of CML and/or CMA (preferably CML and CMA) is the same or increased when compared to an ASD reference standard. Preferably the sample is a blood plasma ultrafiltrate sample.

In one embodiment the concentration of GSA and/or pyrraline (preferably GSA and pyrraline) is increased when compared to a non-ASD reference standard. In one embodiment the concentration of GSA and/or pyrraline (preferably GSA and pyrraline) is the same or increased when compared to an ASD reference standard. Preferably the sample is a urine sample.

In one embodiment the amino acid adduct concentration profiles indicated above indicate the presence of ASD (e.g. said concentration profiles are correlated to the presence of ASD). The skilled person will appreciate that where the amino acid adduct concentration profiles detailed above are not detected, that this preferably indicates the absence of ASD.

In one embodiment, the term "one or more" when used in the context of an amino acid adduct described herein means at least 1, 2, 3, 4, 5, 6, 7, 8, 9, 10, or 11, of the amino acid adducts.

In one embodiment, the term "one or more" when used in the context of an amino acid adduct described herein means at least 1, 2, 3, 4, 5, 6, 7, 8, 9, 10, 11, 12, 13, 14, or 15 of the amino acid adducts.

In a preferred embodiment, the term "one or more" when used in the context of an amino acid adduct described herein means at least 2 of the amino acid adducts.

In a particularly preferred embodiment, the term "one or more" when used in the context of an amino acid adduct described herein means all (e.g. a combination of each) of the amino acid adducts.

The present inventors have found that certain amino acid adducts may be substituted by those amino acid adducts correlated thereto (see FIG. 17-21). A positive correlation between amino acid adducts indicates that as the concentration of one of the amino acid adducts increases the concentration of the other amino acid adduct also increases; whereas a negative correlation between amino acid adducts indicates that as the concentration of one of the amino acid adducts increases the other decreases. The skilled person can therefore choose suitable correlating amino acid adducts to substitute those recited above, and can determine whether said amino acid will increase or decrease in concentration relative to a reference standard as indicated by a positive or negative correlation. In one embodiment an appropriate scaling constant is determined and applied to the substituted amino acid adduct.

For example, the amino acid adducts may be correlated (and substituted) as indicated in the table below:

| Source | Amino acid adduct | Positively Correlated Analyte | Negatively Correlated Analyte |
| --- | --- | --- | --- |
| Plasma | CML | DT | |
| | 3DG-H | — | |
| | CMA | MG-H1, DT | |
| | DT | G-H1 | |
| Plasma filtrate | CML | FL | |
| | CMA | CEL, AASA, MG-H1, FL | MOLD |
| | G-H1 | | |
| | GSA | — | |
| Urine | Pyrraline | CML, MG-H1, CMA, DT, GSA | |
| | GSA | Pyrraline, FL, CML, CMA, DT, AASA | |

The reference standard may be an ASD reference standard or a non-ASD reference standard.

A "non-ASD reference standard" refers a sample obtained from a subject that does not have ASD (e.g. a healthy subject). For example, a "non-ASD reference standard" may be obtained from a subject who has not been diagnosed with ASD and does not exhibit a symptom of ASD.

Alternatively, an "ASD reference standard" refers to a sample obtained from a subject that has ASD. For example, an "ASD reference standard" may be obtained from a subject who has been diagnosed with ASD and exhibits one or more symptoms of ASD. Such diagnosis may have been performed using one or more conventional methods, such as on the basis of a clinician's perception of symptoms in the patient, where scores derived from assessment of patient performance in standardized activities are used, including Autism Diagnostic Observation Schedule (ADOS) score, the childhood autism rating scale (CARS), checklist for autism in toddlers (CHAT) and social communication questionnaire (SCQ).

The reference standard used in a method of the invention may be age and/or gender matched to the subject from which the sample to be used in a method of the invention is obtained.

In one embodiment a method of the invention is carried out in combination with one of the above-referenced conventional ASD diagnostic methods.

The detected concentration of an amino acid adduct in the reference standard may have been obtained (e.g. quantified) previously to a method of the invention.

The reference standard is preferably derived from the same sample type as the sample type that is being tested, thus allowing for an appropriate comparison between the two (or more). Thus, by way of example, if the sample is derived from urine, the reference standard is also derived from urine. Alternatively, if the sample is a blood sample (e.g. a plasma or a serum sample), then the reference standard will also be a blood sample (e.g. a plasma sample or a serum sample, as appropriate).

When comparing between the sample and the reference standard, the way in which the concentrations are expressed is matched between the sample and the reference standard. Thus, an absolute concentration can be compared with an absolute concentration, and a relative concentration can be compared with a relative concentration. Similarly, the way in which the concentrations are expressed for classification with a diagnostic algorithm (as described below) is matched to the way in which the concentrations are expressed for training the diagnostic algorithm.

In one embodiment, the concentrations of the amino acid adducts are normalised to the concentration of creatinine detected in the same sample.

In one embodiment, the concentrations of amino acid adducts are normalised to their amino acid residue (e.g. unmodified amino acid residue) precursors and preferably expressed as mmol amino acid adduct per mol (mmol/mol) amino acid.

The reference standards may be obtained either within (i.e. constituting a step of) or external to the (i.e. not constituting a step of) methods of the invention. In one embodiment, the methods of the invention may comprise a step of obtaining a reference standard. In one embodiment, the reference standards are obtained externally to the method of the invention and accessed during the comparison step of the invention.

In one embodiment, the reference standard is the concentration of an amino acid adduct in a sample or samples derived from one subject. Alternatively, the reference standard may be derived by pooling data obtained from multiple subjects, and calculating an average (for example, mean or median) concentration for each amino acid adduct. Thus, the reference standard may reflect the average concentration of an amino acid adduct in multiple subjects.

In some embodiments, detecting the concentration of an amino acid adduct in a sample encompasses detecting the absence of the amino acid adduct in the sample.

Detecting the presence or absence of a concentration of an amino acid adduct (or amino acid) difference correlates with the presence or absence of ASD.

In embodiments where the reference standard is a non-ASD reference standard detecting the presence of a concentration difference may indicate the presence of ASD, and detecting the absence of a concentration difference may indicate the absence of ASD. However, where an increased concentration of an amino acid adduct when compared to a non-ASD reference standard has been established to correlate with the presence of ASD, the skilled person will understand that a decrease (or no change) in said concentration when compared to the non-ASD reference standard may not be indicative of the presence of ASD. Likewise, where a decreased concentration of an amino acid adduct when compared to a non-ASD reference standard has been established to correlate with the presence of ASD, the skilled person will understand that an increase (or no change) in said concentration when compared to the non-ASD reference standard may not be indicative of the presence of ASD.

In embodiments where the reference standard is an ASD reference standard, detecting the presence of a concentration difference may indicate the absence of ASD, and detecting the absence of a concentration difference may indicate the presence of ASD. However, where an increased concentration of an amino acid adduct (or amino acid) when compared to a non-ASD reference standard has been established to correlate with the presence of ASD, the skilled person will understand that a(n) (further) increase in said concentration when compared to the ASD reference standard may still be indicative of the presence of ASD. Likewise, where a decreased concentration of an amino acid adduct (or amino acid) when compared to a non-ASD reference standard has been established to correlate with the presence of ASD, the skilled person will understand that a (further) decrease in said concentration when compared to the ASD reference standard may still be indicative of the presence of ASD.

In a related aspect, there is provided a method for diagnosing an autistic spectrum disorder (ASD), said method comprising:
a. detecting the concentration of an amino acid adduct in a sample obtained from a subject, wherein said amino acid adduct is a glycated amino acid adduct, an oxidised amino acid adduct, or a nitrated amino acid adduct; and
b. classifying the health of the subject based on the concentration of the amino acid adduct detected in the sample with a diagnostic algorithm, wherein the diagnostic algorithm is trained on the corresponding concentration for the same amino acid adduct obtained from a population of subjects having known disease status, and thereby diagnosing the presence or absence of ASD in the subject.

In one embodiment, this aspect of the invention uses a diagnostic algorithm developed via a machine learning approach and which is trained by two fold cross-validation e.g. trained based on the concentration of an amino acid adduct detected in 50% of the ASD and non-ASD (control) subjects (training subset) before being used to predict the disease status for the remaining 50% of subjects (test set)—see for example FIG. 2.

In one embodiment, this aspect of the invention uses a 2-class diagnostic algorithm developed via a machine learning approach and which is trained based on the concentration of an amino acid adduct in a sample from a known ASD subject and known non-ASD subject, before being used to classify the health of a test subject.

By testing a panel of different amino acid adducts the present inventors have identified various subsets of amino acid adducts that provide highly sensitive and specific determination of the presence or absence of ASD in a subject. As demonstrated in Example 5 and FIGS. 13 and 14, this method of the invention allows for the diagnosis of presence or absence of ASD in the subject with a high level of sensitivity and specificity.

The term "disease status" may be used synonymously with "ASD status" (i.e. the status of presence or absence of ASD in a subject).

As used herein, the phrase "classifying the health of the subject based on the concentration the amino acid detected in the sample with a diagnostic algorithm" refers to the statistical or machine learning classification process by which the concentration of the amino acid adduct in the test sample is used to determine a category of health with a diagnostic algorithm, typically a statistical or machine learning classification algorithm. The term "classifying the health of the subject" as used herein refers to classifying the subject as having ASD, or alternatively classifying the subject as not having ASD.

Classification by a diagnostic algorithm may include scoring likelihood of a panel of amino acid adduct concentrations belonging to each possible category, and determining the highest-scoring category. Classification by a diagnostic algorithm may include comparing a panel of amino acid adduct concentrations to previous observations by means of a distance function. Examples of diagnostic algorithms suitable for classification include support vector machines, ensemble classifier algorithms, random forests, logistic regression (e.g. multiclass or multinomial logistic regression, and/or algorithms adapted for sparse logistic regression). A wide variety of other diagnostic algorithms that are suitable for classification may be used, as known to a person skilled in the art.

In one embodiment, the phrase "training the diagnostic algorithm" may refer to supervised learning of a diagnostic algorithm on the basis of concentrations for each amino acid adduct obtained from a population of subjects having known ASD health. The phrase "training the diagnostic algorithm" may refer to variable selection in a statistical model on the basis of concentrations for each amino acid adduct obtained from a population of subjects having known ASD health. Training a diagnostic algorithm may for example include determining a weighting vector in feature space for each category, or determining a function or function parameters.

As used herein, the term "population of subjects" means one or more subjects. In one embodiment, the population of subjects consists of one subject. In one embodiment, the population of subjects comprises multiple subjects. As used herein, the term "multiple" means at least 2 (such as at least 4, 6, 8, 10, 12, 14, 16, 18, 20, 22, 24, 26, 28, or 30) subjects. In one embodiment, the population of subjects comprises at least 30 subjects.

The training of a diagnostic algorithm may be obtained either within (i.e. constituting a step of) or external to (i.e. not constituting a step of) the methods of the invention. In one embodiment, the methods of the invention may comprise a step of training of a diagnostic algorithm. In one embodiment, the diagnostic algorithm is trained externally to the method of the invention and accessed during the classification step of the invention.

The diagnostic algorithm may be trained by detecting the concentration of an amino acid adduct in a sample obtained from a population of healthy subject(s). As used herein, the term "healthy subject" refers to an individual subject or group of subjects who have not shown any symptoms of ASD, have not been diagnosed with ASD and/or are not likely to develop ASD. Preferably said healthy subject(s) is not on medication affecting the disease and has not been diagnosed with any other disease. The one or more healthy subjects may have a similar sex, age and body mass index (BMI) as compared with the test subject.

The diagnostic algorithm may be trained by detecting the concentration of an amino acid adduct in a sample obtained from a population of subject(s) suffering from ASD. More preferably such subject(s) may have similar sex, age and body mass index (BMI) as compared with the test subject.

Once the amino acid adduct concentration profile characteristic of ASD is determined (providing a reference profile), the profile of concentrations from a sample obtained from a subject may be compared to this reference profile to determine whether the test subject also has ASD. Once the diagnostic algorithm is trained to classify ASD, the profile of concentrations from a sample obtained from a subject may be classified by the diagnostic algorithm to determine whether the test subject also has ASD.

In one embodiment, when performing the method for diagnosing ASD, the population of subjects used to obtain reference standards for the diagnostic algorithm, and/or the population of subjects used to train the diagnostic algorithm, may comprise: at least one (healthy) subject having no ASD, and/or at least one subject having ASD. In one embodiment, the population of subjects may comprise: multiple (e.g. at least 10) (healthy) subjects having no ASD, and/or multiple (e.g. at least 10) subjects having ASD.

By comparing the concentration of an amino acid adduct in a sample obtained from a test subject to the concentration of an amino acid adduct for a reference standard obtained from a population of subjects having known ASD health (e.g. known to have ASD and/or known not to have ASD), it is possible to determine the ASD health of the subject.

By classifying the health based on the concentration of an amino acid adduct with a diagnostic algorithm trained on corresponding concentration obtained from a population of subjects having known health, it is possible to determine whether a subject has or does not have ASD. The method permits classification of the subject as belonging to or not belonging to the reference population (i.e. by determining whether the concentration of amino acid adducts in the subject are statistically similar to the reference population or statistically deviate from the reference population). Hence, classification of the subject's concentration profile (i.e. the overall pattern of change observed for the concentrations detected) as corresponding to the profile derived from a particular reference population predicts that the subject falls (or does not fall) within the reference population.

In one embodiment, a subject may be diagnosed as having ASD when the concentration of amino acid adducts detected is statistically similar to the concentration determined for the corresponding amino acid adduct concentrations detected in a population of subjects having ASD. In one embodiment, a subject may be diagnosed as having no ASD when the concentration of amino acid adducts detected is statistically similar to the amount determined for the corresponding values obtained from a population of subjects having no ASD.

As used herein, the term "statistically similar" means that the concentrations of the amino acid adducts detected for the test subject are similar to those detected for the reference population to a statistically significant level. The term "statistically significant" means that the alteration is greater than what might be expected to happen by chance alone (e.g. p=<0.05). Statistical significance can be determined by any method known in the art.

In one embodiment, a subject may be diagnosed as having ASD when the concentrations of the amino acid adducts detected statistically deviates from the amount determined for the corresponding values obtained from a population of subjects having no ASD. In one embodiment, a subject may be diagnosed as having no ASD when the concentration of the amino acid adduct detected statistically deviates from the concentration determined for the corresponding amino acid adduct obtained from a population of subjects having ASD.

As used herein, the term "statistically deviates" means that the concentrations of the amino acid adducts detected for the test subject differs from those detected for the reference population to a statistically significant level. The deviation in marker abundance may be an increase or decrease.

Thus, classification of the subject in methods of the invention may be performed using a diagnostic algorithm. The diagnostic algorithm used in the method of the invention is a classification algorithm. In one embodiment, the classification algorithm comprises a support vector machine algorithm. In one embodiment, the classification algorithm is an ensemble algorithm comprising different types of classification algorithms. In one embodiment, the classification algorithm comprises a decision tree based algorithm. Other types of algorithms, such as regression algorithms and neural networks, may also be used. In one embodiment, the classification algorithm comprises a random forest algorithm.

Classification of the subjects by the diagnostic algorithm does not require perfect classification. Classification may be characterized by its "sensitivity." The "sensitivity" of classification relates to the percentage of subjects who were correctly identified as having ASD. "Sensitivity" is defined in the art as the number of true positives divided by the sum of true positives and false negatives.

The sensitivity of the methods of the invention may be at least about 65%, 70%, 75%, 77%, 80%, 85%, 86%, 87%, 88%, 89%, 90%, or 92%.

The "specificity" of the methods of the invention is defined as the percentage of patients who were correctly identified as not having ASD. "Specificity" relates to the number of true negatives divided by the sum of true negatives and false positives. The specificity of the methods of the invention may be at least about 67%, 70%, 75%, 80%, 84%, 86%, 87%, 88%, 89%, or 90%.

The invention also provides a computational model based on a diagnostic algorithm adapted to classify the health of a subject based on the concentration of an amino acid adduct detected in the sample with a diagnostic algorithm, wherein the diagnostic algorithm is trained on the corresponding concentration for the amino acid adduct obtained from a population of subjects having known disease status. The invention also extends to software adapted to produce a computational model as aforementioned. The invention also extends to a processor adapted to produce a computational model as aforementioned.

In a further aspect, the invention provides a method for treating an autistic spectrum disorder (ASD) in a subject, comprising:

a. detecting the concentration of an amino acid adduct in a sample obtained from a subject, wherein said amino acid adduct is a glycated amino acid adduct, an oxidised amino acid adduct, or a nitrated amino acid adduct;
b. comparing the concentration of the amino acid adduct in the sample with the concentration of the same amino acid adduct in a reference standard; and
c. identifying the presence or absence of a concentration difference of said amino acid adduct in the sample relative to the reference standard;
   wherein the presence or absence of a concentration difference correlates with the presence or absence of ASD; and
d. administering to a subject diagnosed with ASD a therapy for ASD.

The invention also provides a method for treating an autistic spectrum disorder (ASD) in a subject, said method comprising:
a. detecting the concentration of an amino acid adduct in a sample obtained from a subject, wherein said amino acid adduct is a glycated amino acid adduct, an oxidised amino acid adduct, or a nitrated amino acid adduct; and
b. classifying the health of the subject based on the concentration the amino acid adduct detected in the sample with a diagnostic algorithm, wherein the diagnostic algorithm is trained on the corresponding concentration for the same amino acid adduct obtained from a population of subjects having known disease status, and thereby diagnosing the presence or absence of ASD in the subject; and
c. administering to a subject diagnosed with ASD a therapy for ASD.

In one embodiment, this aspect of the invention uses a diagnostic algorithm developed via a machine learning approach and which is trained by two fold cross-validation e.g. trained based on the concentration of an amino acid adduct detected in 50% of the ASD and non-ASD (control) subjects (training subset) before being used to predict the disease status for the remaining 50% of subjects (test set)—see for example FIG. 2.

In one embodiment said method uses a 2-class diagnostic algorithm developed via a machine learning approach and which is trained based on the concentration of an amino acid adduct in a sample from a known ASD subject and known non-ASD subject, before being used to classify the health of a test subject.

By testing a panel of different amino acid adducts the present inventors have identified various subsets of markers that provide highly sensitive and specific determination the presence or absence of ASD in a subject. As demonstrated in Example 5 and FIGS. 13 and 14, this method of the invention allows for the diagnosis of presence or absence of ASD in the subject with a high level of sensitivity and specificity.

The methods of the invention are intended to encompass all known treatments for ASD. The skilled person will be familiar with treatments for ASD.

In one aspect the invention provides a method for identifying a therapy suitable for treating ASD, said method comprising:
a. providing an isolated sample from a subject administered a candidate therapy;
b. detecting the concentration of an amino acid adduct in said sample, wherein said amino acid adduct is a glycated amino acid adduct, an oxidised amino acid adduct, or a nitrated amino acid adduct;
c. determining the relative concentration change of the amino acid adduct by comparing the concentration of the amino acid adduct detected in step (b) with the concentration of the amino acid adduct in an isolated sample from the subject prior to administration of the candidate therapy; and
   wherein the candidate therapy is suitable for treating ASD when a concentration change is detected after administering the candidate therapy; and
   wherein the candidate therapy is not suitable for treating ASD when a concentration change is not detected after administering the candidate therapy.

Another aspect provides a method for monitoring the efficacy of an ASD therapy, said method comprising:
a. providing an isolated sample from a patient administered said therapy;
b. detecting the concentration of an amino acid adduct in said sample, wherein said amino acid adduct is a glycated amino acid adduct, an oxidised amino acid adduct, or a nitrated amino acid adduct;
c. determining the relative concentration change of the amino acid adduct by comparing the concentration of the amino acid adduct detected in step (b) with the concentration of the amino acid adduct in an isolated sample from the subject at an earlier timepoint; and
   confirming the presence of efficacy when a concentration change is detected; and
   confirming the absence of efficacy when a concentration change is not detected.

The term "earlier timepoint" may refer to a timepoint of at least 24 hours, at least 48 hours, at least 72 hours, at least 96 hours, at least 120 hours, at least 1 week, at least 2 weeks, at least 3 weeks, at least 4 weeks, at least 8 weeks, at least 12 weeks, at least 16 weeks, at least 20 weeks, at least 30 weeks, at least 40 weeks, at least 52 weeks, at least 2 years, at least 3 years, or at least 4 years earlier.

The invention provides in another aspect use a glycated amino acid adduct, an oxidised amino acid adduct, a nitrated amino acid adduct, or a combination thereof for:
a. diagnosing ASD;
b. determining prognosis of ASD;
c. identifying a therapy suitable for treating ASD;
d. monitoring efficacy of an ASD therapy; and/or
e. use as a feature in an ASD diagnostic algorithm.

In one embodiment, an amino acid adduct is one or more selected from $N_\varepsilon$-fructosyl-lysine (FL), glyoxal-derived hydroimidazolone (G-H1), 3-deoxyglucosone-derived hydroimidazolone (3DG-H), $N_\varepsilon$-carboxymethyl-lysine (CML), $N_\omega$-carboxymethylarginine (CMA), methylglyoxal-derived hydroimidazolone (MG-H1), pyrraline and/or methylglyoxal-derived lysine dimer (MOLD), dityrosine (DT), N-formylkynurenine (NFK), α-aminoadipic semialdehyde (AASA), and glutamic semialdehyde (GSA) (preferably one or more selected from FL, G-H1, 3DG-H, CML, CMA, MG-H1, pyrraline and/or MOLD, NFK, AASA, and GSA).

In one embodiment, an amino acid adduct is one or more selected from 3-deoxyglucosone-derived hydroimidazolone (3DG-H), $N_\varepsilon$-carboxymethyl-lysine (CML), $N_\omega$-carboxymethylarginine (CMA), dityrosine (DT), and glutamic semialdehyde (GSA) (preferably one or more selected from 3DG-H, CML, CMA, and GSA).

In one embodiment, the concentration of one or more amino acid adduct selected from: $N_\varepsilon$-carboxymethyl-lysine (CML), $N_\omega$-carboxymethylarginine (CMA), methylglyoxal-derived hydroimidazolone (MG-H1), α-aminoadipic semialdehyde (AASA), glyoxal-derived hydroimidazolone (G-H1), methylglyoxal-derived lysine dimer (MOLD), pyrraline, N-formylkynurenine (NFK), α-aminoadipic semialdehyde (AASA), glutamic semialdehyde (GSA) and dityrosine (DT) (preferably one or more selected from CML, CMA, MG-H1, AASA, G-H1, MOLD, pyrraline, NFK, AASA and GSA) is increased in the sample when compared to a non-ASD reference standard. The person skilled in the art appreciates that where the detected concentration is the same or less than the concentration in a non-ASD reference standard, ASD is not diagnosed.

In one embodiment, the concentration of one or more amino acid adduct selected from: 3-deoxyglucosone-derived hydroimidazolone (3DG-H), $N_\varepsilon$-fructosyl-lysine (FL), glyoxal-derived hydroimidazolone (G-H1), N-formylkynurenine (NFK) and glucosepane (GSP) is decreased in the sample when compared to a non-ASD reference standard. The person skilled in the art appreciates that where the detected concentration is the same or more than the concentration in a non-ASD reference standard, ASD is not diagnosed.

As demonstrated in Example 5 and FIGS. 13 and 14, a number of the amino acid adducts described herein have been identified as particularly useful for ensuring diagnostic performance of an algorithm of the invention.

Thus, in one embodiment, the amino acid adduct is one or more selected from glyoxal-derived hydroimidazolone (G-H1), 3-deoxyglucosone-derived hydroimidazolone (3DG-H), $N_\varepsilon$-carboxymethyl-lysine (CML), $N_\omega$-carboxymethylarginine (CMA), pyrraline, dityrosine (DT), α-aminoadipic semialdehyde (AASA) and glutamic semialdehyde (GSA) (preferably one or more selected from G-H1, 3DG-H, CML, CMA, pyrraline, AASA, and GSA).

In one embodiment, the amino acid adduct is one or more selected from $N_\varepsilon$-carboxymethyl-lysine (CML), $N_\omega$-carboxymethylarginine (CMA), 3-deoxyglucosone-derived hydroimidazolone (3DG-H), and dityrosine (DT) (preferably one or more selected from CML, CMA, and 3DG-H).

In one embodiment, the amino acid adduct is one or more selected from $N_\varepsilon$-carboxymethyl-lysine (CML) and $N_\omega$-carboxymethylarginine (CMA).

In one embodiment, the amino acid adduct is one or more selected from $N_\varepsilon$-carboxymethyl-lysine (CML), $N_\omega$-carboxymethylarginine (CMA), 3-deoxyglucosone-derived hydroimidazolone (3DG-H), glyoxal-derived hydroimidazolone (G-H1), dityrosine (DT), and glutamic semialdehyde (GSA) (preferably one or more selected from CML, CMA, 3DG-H, G-H1 and GSA).

In one embodiment, the amino acid adduct is one or more pyralline and glutamic semialdehyde (GSA).

As demonstrated in Example 2 and FIGS. 4 and 12A, a number of the amino acid adducts comprised within a polypeptide sequence described herein have been identified as having particular statistical significance in the diagnosis of ASD when detected in blood plasma samples.

Thus, in one embodiment, the concentration of one or more amino acid adduct selected from: $N_\varepsilon$-fructosyl-lysine (FL), $N_\varepsilon$-carboxymethyl-lysine (CML), glyoxal-derived hydroimidazolone (G-H1), methylglyoxal-derived hydroimidazolone (MG-H1), $N_\omega$-carboxymethylarginine (CMA), glucosepane (GSP), dityrosine (DT) and glutamic semialdehyde (GSA) (preferably one or more selected from FL, CML, G-H1, MG-H1, CMA, GSP, and GSA) is increased in the sample when compared to a non-ASD reference standard.

In one embodiment, the concentration of one or more amino acid adduct selected from $N_\varepsilon$-carboxymethyl-lysine (CML), $N_\omega$-carboxymethylarginine (CMA), methylglyoxal-derived hydroimidazolone (MG-H1) and dityrosine (DT) (preferably one or more selected from CML, CMA, and MG-H1) is increased in the sample when compared to a non-ASD reference standard.

In one embodiment, the concentration of one or more amino acid adduct selected from $N_\varepsilon$-carboxymethyl-lysine (CML), $N_\omega$-carboxymethylarginine (CMA) and dityrosine (DT) (preferably one or more selected from CML, and CMA) is increased in the sample when compared to a non-ASD reference standard.

In one embodiment, the concentration of one or more amino acid adduct selected from $N_\varepsilon$-(1-carboxyethyl)lysine (CEL), 3-deoxyglucosone-derived hydroimidazolone (3DG-H), methylglyoxal-derived lysine dimer (MOLD), N-formylkynurenine (NFK), α-aminoadipic semialdehyde (AASA) or 3-Nitrotyrosine (3-NT) is decreased in the sample when compared to a non-ASD reference standard.

In one embodiment, the concentration of amino acid adduct is 3-deoxyglucosone-derived hydroimidazolone (3DG-H) is decreased in the sample when compared to a non-ASD reference standard.

In one embodiment, the concentration of one or more amino acid adduct selected from: $N_\varepsilon$-carboxymethyl-lysine (CML), $N_\omega$-carboxymethylarginine (CMA), methylglyoxal-derived hydroimidazolone (MG-H1), and dityrosine (DT) (preferably one or more selected from CML, CMA, and MG-H1) is increased in the sample when compared to a non-ASD reference standard and the concentration of the amino acid adduct 3-deoxyglucosone-derived hydroimidazolone (3DG-H) is decreased in the sample when compared to a non-ASD reference standard.

In one embodiment, the concentration of one or more amino acid adduct selected from: $N_\varepsilon$-carboxymethyl-lysine (CML), $N_\omega$-carboxymethylarginine (CMA); and dityrosine (DT) (preferably one or more selected from CML and CMA) is increased in the sample when compared to a non-ASD reference standard and the concentration of the amino acid adduct 3-deoxyglucosone-derived hydroimidazolone (3DG-H) is decreased in the sample when compared to a non-ASD reference standard.

As demonstrated in Example 3 and FIGS. 5 and 12B, a number of the amino acid adducts described herein have been identified as showing particular statistical significance in the diagnosis of ASD when detected in blood plasma samples (e.g. blood plasma ultrafiltrate).

In one embodiment, the concentration of one or more amino acid adduct selected from: $N_\varepsilon$-carboxymethyl-lysine (CML), $N_\varepsilon$-(1-carboxyethyl)lysine (CEL), methylglyoxal-derived hydroimidazolone (MG-H1), $N_\omega$-carboxymethyl-arginine (CMA), glucosepane (GSP), dityrosine (DT), α-aminoadipic semialdehyde (AASA), glutamic semialdehyde (GSA), and 3-Nitrotyrosine (3-NT) (preferably one or more selected from CML, CEL, MG-H1, CMA, GSP, AASA, GSA and 3-NT) is increased in the sample when compared to a non-ASD reference sample.

In one embodiment, the concentration of one or more amino acid adduct selected from: $N_\omega$-carboxymethylarginine (CMA), α-aminoadipic semialdehyde (AASA) and glutamic semialdehyde (GSA) is increased in the sample when compared to a non-ASD reference sample.

In one embodiment, the concentration of the amino acid is $N_\omega$-carboxymethylarginine (CMA) is increased in the sample when compared to a non-ASD reference sample.

In one embodiment, the concentration of one or more amino acid adduct selected from: $N_\varepsilon$-fructosyl-lysine (FL), glyoxal-derived hydroimidazolone (G-H1), 3-deoxyglucosone-derived hydroimidazolone (3DG-H), methylglyoxal-derived lysine dimer (MOLD) and N-formylkynurenine (NFK) is decreased in the sample when compared to a non-ASD reference sample.

In one embodiment, the concentration of one or more amino acid adduct selected from: $N_ε$-fructosyl-lysine (FL), glyoxal-derived hydroimidazolone (G-H1), and N-formylkynurenine (NFK) is decreased in the sample when compared to a non-ASD reference sample.

In one embodiment, the concentration of the amino acid adduct glyoxal-derived hydroimidazolone (G-H1) is decreased in the sample when compared to a non-ASD reference standard.

In one embodiment, the concentration of one or more amino acid adduct selected from: $N_ω$-carboxymethylarginine (CMA), α-aminoadipic semialdehyde (AASA) and glutamic semialdehyde (GSA) is increased in the sample when compared to a non-ASD reference standard and the concentration of one or more amino acid adduct selected from: $N_ε$-fructosyl-lysine (FL), glyoxal-derived hydroimidazolone (G-H1) and N-formylkynurenine (NFK) is decreased in the sample when compared to a non-ASD reference standard.

In one embodiment, the concentration of the one or more amino acid adduct selected from $N_ε$-carboxymethyl-lysine (CML) and $N_ω$-carboxymethylarginine (CMA) is increased in the sample when compared to a non-ASD reference standard and the concentration of the amino acid adduct glyoxal-derived hydroimidazolone (G-H1) is decreased in the sample when compared to a non-ASD reference standard.

As demonstrated in Example 4 and FIGS. 6 and 12C, a number of the amino acid adducts described herein have been identified as showing particular statistical significance in the diagnosis of ASD when detected in urine samples (e.g. urine ultrafiltrate).

In one embodiment, the concentration of one or more amino acid adduct selected from: $N_ε$-fructosyl-lysine (FL), $N_ε$-carboxymethyl-lysine (CML), $N_ε$-(1-carboxyethyl)lysine (CEL), glyoxal-derived hydroimidazolone (G-H1), methylglyoxal-derived hydroimidazolone (MG-H1), 3-deoxyglucosone-derived hydroimidazolone (3DG-H), $N_ω$-carboxymethylarginine (CMA), methylglyoxal-derived lysine dimer (MOLD), dityrosine (DT), N-formylkynurenine (NFK), α-aminoadipic semialdehyde (AASA), glutamic semialdehyde (GSA), and 3-Nitrotyrosine (3-NT) (preferably one or more selected from FL, CML, CEL, G-H1, MG-H1, 3DG-H, CMA, MOLD, NFK, AASA, GSA, and 3-NT) is increased in the sample when compared to a non-ASD reference standard.

In one embodiment, the concentration of one or more amino acid adduct selected from: $N_ε$-carboxymethyl-lysine (CML), glyoxal-derived hydroimidazolone (G-H1), $N_ω$-carboxymethylarginine (CMA), methylglyoxal-derived lysine dimer (MOLD), pyrraline, dityrosine (DT), N-formylkynurenine (NFK), α-aminoadipic semialdehyde (AASA) and glutamic semialdehyde (GSA) (preferably one or more selected from CML, G-H1, CMA, MOLD, pyrraline, NFK, AASA, and GSA) is increased in the sample when compared to a non-ASD reference standard.

In one embodiment, the concentration of one or more amino acid adduct selected from: dityrosine (DT) and glutamic semialdehyde (GSA) (preferably GSA) is increased in the sample when compared to a non-ASD reference standard.

In one embodiment, the amino acid adduct glucosepane (GSP) is decreased in the sample when compared to a non-ASD reference standard.

In one embodiment, the concentration of one or more amino acid adduct selected from $N_ε$-carboxymethyl-lysine (CML), glyoxal-derived hydroimidazolone (G-H1), $N_ω$-carboxymethylarginine (CMA), methylglyoxal-derived lysine dimer (MOLD), pyrraline, dityrosine (DT), N-formylkynurenine (NFK), α-aminoadipic semialdehyde (AASA) and glutamic semialdehyde (GSA) (preferably one or more selected from CML, G-H1, CMA, MOLD, pyrraline, NFK, AASA, and GSA) is increased in the sample when compared to a non-ASD reference standard and the concentration of the amino acid adduct glucosepane (GSP) is decreased in the sample when compared to a non-ASD reference standard.

In one embodiment the amino acid adduct concentration profiles indicated above indicate the presence of ASD (e.g. said concentration profiles are correlated to the presence of ASD). The skilled person will appreciate that where the amino acid adduct concentration profiles detailed above are not detected, that this preferably indicates the absence of ASD.

Insight into renal handling of amino acids by the kidney is gained by deducing the renal clearance (CL) from amino acid concentrations in plasma and urine. For low molecular weight metabolites such as amino acids, CL is believed to be mainly influenced by renal tubule re-uptake of amino acids mediated by amino acid membrane transporters.

In one embodiment, renal clearance amino acid adducts is deduced from the concentration of an amino acid adduct detected in a plasma and urine sample according to the following equation: CL (μl/mg creatinine or ml/mg creatinine)=[Analyte]Urine (nmol/mg creatinine)/[Analyte] Plasma (pmol/ml or nmol/ml).

Thus, in one embodiment, the renal clearance of an amino acid adduct is measured.

As demonstrated in Example 4 and FIGS. 9 and 12D, a number of the amino acid adducts described herein have been identified as having particular statistical significance in the diagnosis of ASD when the renal clearance of said amino acids is detected.

In one embodiment, the renal clearance of the amino acid adduct $N_ω$-carboxymethylarginine (CMA) is decreased when compared to a non-ASD reference standard.

In one embodiment, the renal clearance of an amino acid adduct selected from: dityrosine (DT) and N-formylkynurenine (NFK) (preferably NFK) is increased when compared to a non-ASD reference standard.

Thus, in one embodiment the renal clearance of the amino acid adduct $N_ω$-carboxymethylarginine (CMA) is decreased when compared to a non-ASD reference standard and the renal clearance of an amino acid adduct selected from: dityrosine (DT) and N-formylkynurenine (NFK) (preferably NFK) is increased when compared to a non-ASD reference standard.

In one embodiment the amino acid adduct concentration profiles indicated above indicate the presence of ASD (e.g. said concentration profiles are correlated to the presence of ASD). The skilled person will appreciate that where the amino acid adduct concentration profiles detailed above are not detected, that this preferably indicates the absence of ASD.

Preferably, the methods of the present invention may be in vitro methods (e.g. ex vivo methods). Thus, the invention may be carried out in vitro on an isolated sample that has previously been obtained from a subject.

Suitably, a method or use of the present invention may further comprise the step of recording on a suitable data carrier, the data obtained in the step of detecting the concentration of an amino acid adduct and/or amino acid (as described below) in a sample.

In one aspect, the invention provides a data carrier comprising the data obtained in the step of detecting the concentration of an amino acid adduct and/or amino acid in a sample according to a method or use of the invention. Preferably, said data carrier may be used in a method for diagnosing ASD.

In another aspect, the invention provides a kit comprising reagents for detecting the concentration of an amino acid adduct in a sample, wherein said amino acid adduct is one or more selected from a glycated amino acid adduct, an oxidised amino acid adduct, a nitrated amino acid adduct or a combination thereof; and instructions for use of the same (e.g. in diagnosing ASD).

In one embodiment, a kit of the invention further comprises reagents for detecting the concentration of creatinine in a sample.

In one embodiment, a kit of the invention comprises reagents for detecting the concentration of an amino acid adduct by a method selected from stable isotopic dilution analysis liquid chromatography-tandem mass spectrometry, reaction monitoring (SRM) mass spectrometry, Western Blot, Enzyme-Linked Immunosorbent Assay (ELISA), liquid chromatography mass spectrometry (LC-MS), reverse phase mass spectrometry, surface enhanced laser desorption ionisation time-of-flight mass spectrometry (SELDI-TOF), matrix assisted laser desorption ionisation time-of-flight mass spectrometry (MALDI-TOF), liquid chromatography-tandem mass spectrometry, isotope dilution mass spectrometry, size permeation (gel filtration), ion exchange, affinity, high performance liquid chromatography, ultra performance liquid chromatography, one-dimensional gel electrophoresis (1-DE), and/or two-dimensional gel electrophoresis (2-DE). Preferably, a kit of the invention comprises reagents for detecting the concentration of an amino acid adduct by liquid chromatography-tandem mass spectrometry. More preferably, a kit of the invention comprises reagents for detecting the concentration of an amino acid adduct by liquid chromatography-tandem mass spectrometry.

In one embodiment, the reagent is for detecting the concentration of an amino acid adduct in a sample by isotopic dilution analysis.

In one embodiment, the reagent for quantifying NFK is [$^{15}N_2$]NFK. In one embodiment, the reagent for quantifying DT is ring-[$^2H_6$]DT. In one embodiment, the reagent for quantifying 3-NT is ring-[$^2H_3$]3-NT. In one embodiment, the reagent for quantifying CEL is lysyl-[$^{13}C_6$]CEL. In one embodiment, the reagent for quantifying CML is lysyl-[$^{13}C_6$]CML. In one embodiment, the reagent for quantifying FL is lysyl-[$^{13}C_6$]FL. In one embodiment, the reagent for quantifying CMA is carboxymethyl-[$^{13}C_2$]CMA. In one embodiment, the reagent for quantifying G-H1 is guanidino [$^{15}N_2$]G-H1. In one embodiment, the reagent for quantifying MG-H1 is guanidino-[$^{15}N_2$]MG-H1. In one embodiment, the reagent for quantifying 3DG-H is guanidino-[$^{15}N_2$]3DG-H. In one embodiment, the reagent for quantifying AASA is [$^2H_3$]α-Aminoadipic acid. In one embodiment, the reagent for quantifying GSA is [$^2H_3$]α-Aminoadipic acid. In one embodiment, the reagent for quantifying GSP is [$^{13}C_6$] Glucosepane. In one embodiment, the reagent for quantifying pyrraline is [$^{13}C_6$, $^{15}N_2$] pyrraline. In one embodiment, the reagent for quantifying methylglyoxal-derived lysine dimer (MOLD) is [$^2H_8$]MOLD, e.g. deuterium-MOLD. Alternative stable isotopic substitution may be used in these compounds, as may be selected by those skilled in the art of stable isotopic dilution analysis.

In one embodiment, the reagents for isotopic dilution analysis may comprise at least one (e.g. at least 2, 3, 4, 5, 6, 7, 8, 9, 10, 11, 12 or 13) reagents selected from the group consisting of: [$^{15}N_2$]NFK, ring-[$^2H_6$]DT; ring-[$^2H_3$]3-NT; lysyl-[$^{13}C_6$]CEL, lysyl-[$^{13}C_6$]CML, lysyl-[$^{13}C_6$]FL, carboxymethyl-[$^{13}C_2$]CMA, guanidino [$^{15}N_2$]G-H1, guanidino-[$^{15}N_2$]MG-H1, guanidino-[$^{15}N_2$]3DG-H, [$^2H_3$]α-Aminoadipic acid, [$^{13}C_6$]Glucosepane, and [$^{13}C_6$, $^{15}N_2$] pyrraline.

The kits of the invention may further comprise a known quantity or concentration of the amino acid adducts described herein (or their related stable isotype substituted compounds (isotopomers)) for use as a standard (e.g. reference standard).

The kit of the invention may further comprise instructions for carrying out the methods and uses of the invention as described herein. The kit may further comprise a software licence or key to use software described herein, else said kit may comprise software described herein.

Conventional Amino Acids

The present inventors have also identified a number of amino acids (e.g. conventional or unmodified amino acids) as being useful in the diagnosis of ASD. Said conventional amino acids may be employed alternatively or additionally to the amino acid adducts described above.

All aspects, embodiments and definitions relating to amino acid adducts are also applicable to the following aspects/embodiments, wherein the term "amino acid adduct" is simply to be replaced by "amino acid".

Thus, in one aspect, the present invention provides a method for diagnosing an autistic spectrum disorder (ASD), said method comprising:
a. detecting the concentration of an amino acid in a sample obtained from a subject, wherein said amino acid is one or more selected from a asparagine, glutamate, glutamine, proline, serine, threonine, tryptophan, valine, or a combination thereof, or a combination thereof;
b. comparing the concentration of the amino acid in the sample with the concentration of the same amino acid in a reference standard; and
c. identifying the presence or absence of a concentration difference of said amino acid in the sample relative to the reference standard;
   wherein the presence or absence of a concentration difference correlates with the presence or absence of ASD.

In another aspect, there is provided a method for determining prognosis of an autistic spectrum disorder (ASD), said method comprising:
a. detecting the concentration of an amino acid in a sample obtained from a subject, wherein said amino acid is one or more selected from asparagine, glutamate, glutamine, proline, serine, threonine, tryptophan, valine, or a combination thereof, or a combination thereof;
b. comparing the concentration of the amino acid in the sample with the concentration of the same amino acid in a reference standard; and
c. identifying the presence or absence of a concentration difference of said amino acid in the sample relative to the reference standard;
   wherein the presence or absence of a concentration difference correlates with a good prognosis or a poor prognosis.

In another aspect, there is provided a method for diagnosing an autistic spectrum disorder (ASD), said method comprising:
a. detecting the concentration of an amino acid in a sample obtained from a subject, wherein said amino acid is one or more selected from a asparagine, glutamate, glutamine, proline, serine, threonine, tryptophan, valine, or a combination thereof; and
b. classifying the health of the subject based on the concentration the amino acid detected in the sample with a diagnostic algorithm, wherein the diagnostic algorithm is trained on the corresponding concentration for the same amino acid obtained from a population of subjects having known disease status, and thereby diagnosing the presence or absence of ASD in the subject.

In another aspect, there is provided a method for treating an autistic spectrum disorder (ASD) in a subject, comprising:
a. detecting the concentration of an amino acid in a sample obtained from a subject, wherein said amino acid is one or more selected from asparagine, glutamate, glutamine, proline, serine, threonine, tryptophan, valine, or a combination thereof;
b. comparing the concentration of the amino acid in the sample with the concentration of the same amino acid in a reference standard; and
c. identifying the presence or absence of a concentration difference of said amino acid in the sample relative to the reference standard;
  wherein the presence or absence of a concentration difference correlates with the presence or absence of ASD; and
d. administering to a subject diagnosed with ASD a therapy for ASD.

In another aspect, there is provided a method for treating an autistic spectrum disorder (ASD) in a subject, said method comprising:
a. detecting the concentration of an amino acid in a sample obtained from a subject, wherein said amino acid is one or more selected from asparagine, glutamate, glutamine, proline, serine, threonine, tryptophan, valine, or a combination thereof; and
b. classifying the health of the subject based on the concentration the amino acid detected in the sample with a diagnostic algorithm, wherein the diagnostic algorithm is trained on the corresponding concentration for the same amino acid obtained from a population of subjects having known disease status, and thereby diagnosing the presence or absence of ASD in the subject; and
c. administering to a subject diagnosed with ASD a therapy for ASD.

In another aspect, there is provided a method for identifying a therapy suitable for treating ASD, said method comprising:
a. providing an isolated sample from a subject administered a candidate therapy;
b. detecting the concentration of an amino acid in said sample, wherein said amino acid selected from asparagine, glutamate, glutamine, proline, serine, threonine, tryptophan, or valine;
c. determining the relative concentration change of the amino acid by comparing the concentration of the amino acid detected in step (b) with the concentration of the amino acid in an isolated sample from the subject prior to administration of the candidate therapy; and
  wherein the candidate therapy is suitable for treating ASD when a concentration change is detected after administering the candidate therapy; and
  wherein the candidate therapy is not suitable for treating ASD when a concentration change is not detected after administering the candidate therapy.

In another aspect, there is provided a method for monitoring the efficacy of an ASD therapy, comprising:
a. providing an isolated sample from a patient administered the treatment or therapy;
b. detecting the concentration of an amino acid in said sample, wherein said amino acid is asparagine, glutamate, glutamine, proline, serine, threonine, tryptophan, or valine;
c. determining the relative concentration change of the amino acid by comparing the concentration of the amino acid detected in step (b) with the concentration of the amino acid in an isolated sample from the subject at an earlier timepoint; and
  confirming the presence of efficacy when a concentration change is detected; and
  confirming the absence of efficacy when a concentration change is not detected.

In another aspect, there is provided use of one or more amino acid selected from asparagine, glutamate, glutamine, proline, serine, threonine, tryptophan, valine, or a combination thereof for:
a. diagnosing ASD;
b. determining prognosis of ASD;
c. identifying a therapy suitable for treating ASD;
d. monitoring efficacy of an ASD therapy; and/or
e. use as a feature in an ASD diagnostic algorithm.

Advantageously, changes in the concentration of said amino acids correlate with the presence or absence of ASD.

As demonstrated in Example 3 and FIG. 7, a number of the amino acids described herein have been identified as showing particular statistical significance in the diagnosis of ASD when detected in a plasma ultrafiltrate sample.

Thus, in a preferable embodiment, the amino acid is selected from glutamine, glutamate and/or threonine. In one embodiment, the amino acid is tryptophan.

As demonstrated in Example 4 and FIGS. 8 and 12C, a number of the amino acids described herein have been identified as having particular statistical significance in the diagnosis of ASD when detected in a urine sample.

In one embodiment, the amino acid is a selected from asparagine, proline, serine, tryptophan and/or valine. Preferably, the amino acid may be selected from asparagine, proline, serine, and/or valine.

As demonstrated in Example 4 and FIGS. 9 and 12D, a number of the amino acid adducts described herein have been identified as showing particular statistical significance in the diagnosis of ASD when the renal clearance of said amino acid is detected.

In one embodiment, the amino acid is arginine, glutamine, leucine, phenylalanine, proline or threonine. In one embodiment, the amino acid is glutamine, leucine, phenylalanine, proline or threonine. In another embodiment, the amino acid is tryptophan. In a preferable embodiment, the amino acid is arginine.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an amino acid adduct" includes a plurality of such amino acid adducts and reference to "the amino acid adduct" includes reference to one or more amino acid adducts and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

Abbreviations

AASA, α-aminoadipic semialdehyde; ADOS, autism diagnostic observation schedule; AGE, advanced glycation endproduct; ASD, Autism spectrum disorder; AUROC, area under-the-curve of receiver operating characteristic plot; b0,+AT, solute carrier 7, member 9; CARS, childhood autism rating scale; CAT-3, cationic amino acid transporter-3; CD98hs, cluster of differentiation heavy subunit; CEL, Nε-(1-carboxyethyl)lysine; CL, renal clearance; CMA, Nω-carboxymethylarginine; CML, Nε-carboxymethyl-lysine; 3-DG, 3-deoxyglucosone; 3DG-H, hydroimidazolone AGEs derived from 3-deoxyglucosone; DT, dityrosine; DUOX, dual oxidase; EDTA, ethylenediaminetetra-acetic acid; FL, Nε-fructosyl-lysine; G-H1, hydroimidazolone AGE derived from glyoxal; GSA, glutamic semialdehyde; GSP, glucosepane; hLAT-1, large neutral amino acid transporter subunit-1; LC-MS/MS, liquid chromatography-tandem mass spectrometry; Leiter-R, Leiter international performance scale—revised; MG, methylglyoxal; MG-H1, hydroimidazolone AGE derived from methylglyoxal MOLD, methylglyoxal-derived lysine crosslink; MRM, multiple reaction monitoring; NFK, N-formylkynurenine; 3-NT, 3-nitrotyrosine; PEP-3, psychoeducational profile-3; rBAT, neutral and basic amino acid transport protein; ROS, reactive oxygen species; SLC7A5, solute carrier family 7, member 5; SVM, support vector machines; TD, Typically developing; UPR, unfolded protein response; y+LAT-1, solute carrier family 7 member 7; y+LAT-2, solute carrier family 7 member 6.

FIGURES

Embodiments of the invention will now be described, by way of example only, with reference to the following Figures and Examples.

Figure 1A:
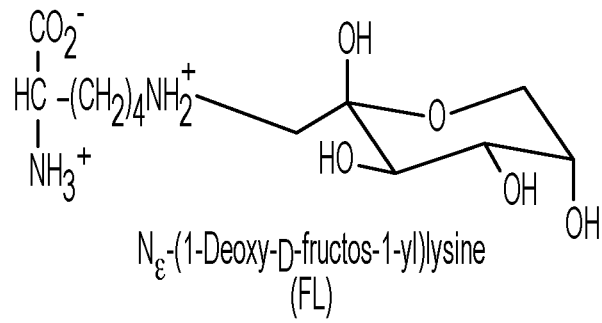
FIG. 1A shows the structure of the early glycation adduct FL. (B) shows the structure of the nitration adduct 3-NT. (C) shows the structure of the advanced glycation endproducts CML, CEL, pyrraline, G-H1, MG-H1, 3DG-H, CMA, Glucosepane and MOLD. (D) shows the structure of the oxidation adducts DT, NFK, 3-NT, AASA and GSA.
Figure 1B:
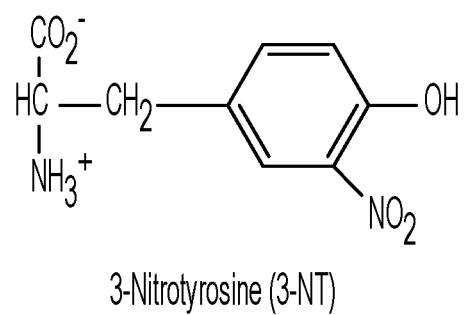
Figure 1C:
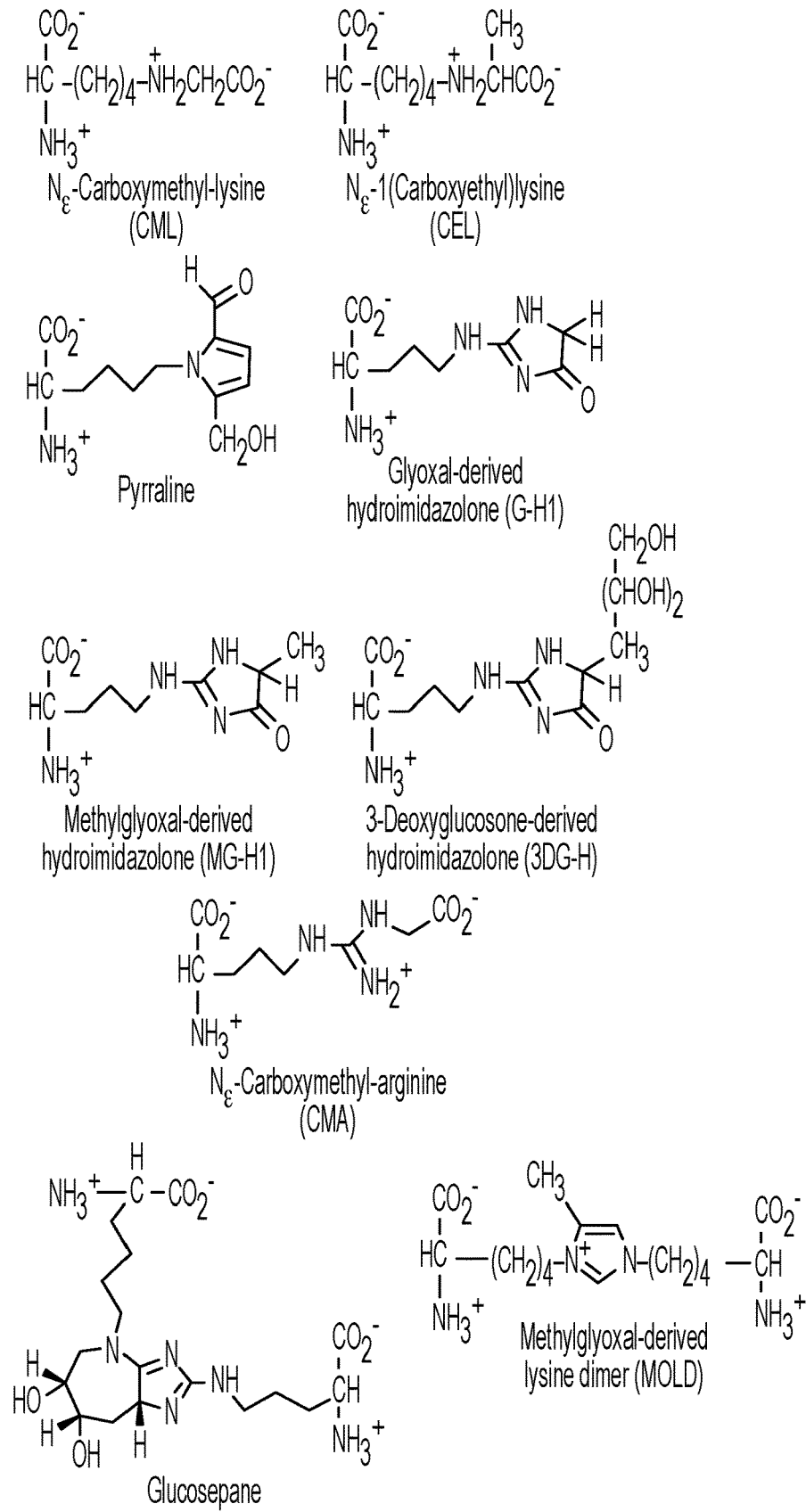
Figure 1D:
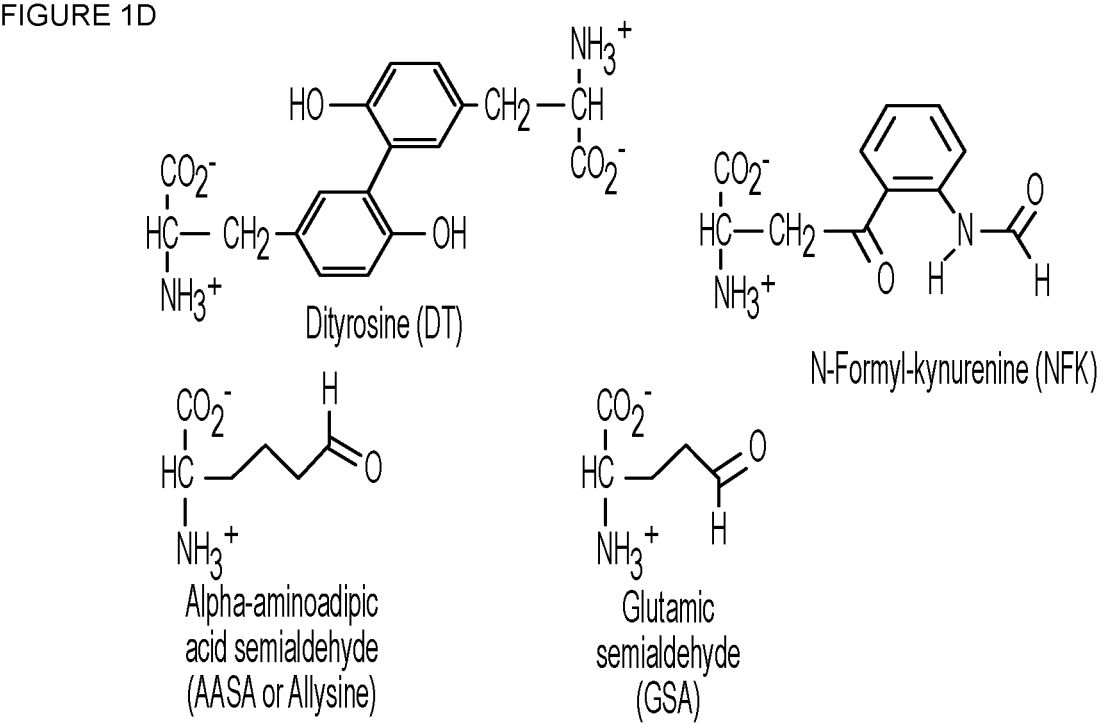

FIG. 3 shows demographic and clinical features of the autistic children group. † Onset pattern was defined according to Ozonoff et. al. (Autism Journal: Official journal of the International Society for Autism Research. 2008; 1(6):320-8) ‡ Probability the subject has autism estimated from diagnostic algorithms derived from the experimental biomarker data (algorithm performance is shown in FIG. 14).

FIG. 4 shows glycation, oxidation and nitration adduct residue content of plasma protein. Data are median (lower-upper quartile); healthy controls, n=21, and ASD, n=27. Significance (Mann-Whitney U); *,  and *, P<0.05, P<0.01 and P<0.001 after Bonferroni correction of 14 applied.

FIG. 5 shows plasma glycation, oxidation and nitration free adduct content in plasma filtrate. Data are median (lower-upper quartile); healthy controls, n=21-31, and ASD, n=27-38. Significance (Mann-Whitney U); *, P<0.05 after Bonferroni correction of 15 applied.

FIG. 6 shows urinary glycation, oxidation and nitration free adduct content. Data are median (lower-upper quartile); healthy controls, n=21-31, and ASD, n=27-38. Significance (Mann-Whitney U); *, P<0.05 after Bonferroni correction of 15 applied.

FIG. 7 shows plasma amino acid metabolome content. Data are Mean±SD or median (lower-upper quartile); healthy controls, n=21, and ASD, n=27. Significance: t-test for parametric data and Mann-Whitney U for non-parametric data. *, p<0.05, **, P<0.01 after Bonferroni correction of 20 applied.

FIG. 8 shows urinary amino acid metabolome content. Data are Mean±SD or median (lower-upper quartile); healthy controls, n=21, and ASD, n=27. Significance: t-test for parametric data and Mann-Whitney U for non-parametric data. *, p<0.05, **, P<0.01 after Bonferroni correction of 20 applied.

FIG. 9 shows renal clearance values of glycation, oxidation and nitration free adducts. Data are mean±SD or median (lower-upper quartile); healthy controls, n=21, and ASD, n=27. Significance: t-test for parametric data and Mann-Whitney U for non-parametric data. *, p<0.05, after Bonferroni correction of 14 applied. # ml/mg creatinine.

FIG. 10 shows renal clearance values of amino acids. Data are mean±SD or median (lower-upper quartile); healthy controls, n=21, and ASD, n=27. Significance: t-test for parametric data and Mann-Whitney U for non-parametric data. *, p<0.05, after Bonferroni correction of 20 applied.

FIG. 11A provides a heatmap illustrating concentration changes of glycation, oxidation and nitration adducts and amino acid metabolome in plasma and urine. (B) A heatmap showing changes of the amino acid metabolome in plasma and urine. The key ($\Delta \log_2$) shown in (A) applies likewise to (B).

FIG. 12 shows data distributions of biomarkers with significantly different changes in the ASD study group after Bonferroni correction. (A) Protein adduct residues CML, CMA and DT. (B) Plasma free adduct CMA. (C) Urine free adducts DT and GSA; and amino acids Asn, Pro, Ser and Val. (D) Renal clearance of CMA and Arg. Significance: one asterisk, two asterisks, and three asterisks indicate P<0.05, P<0.01, and P<0.001, respectively.

Figure 13:
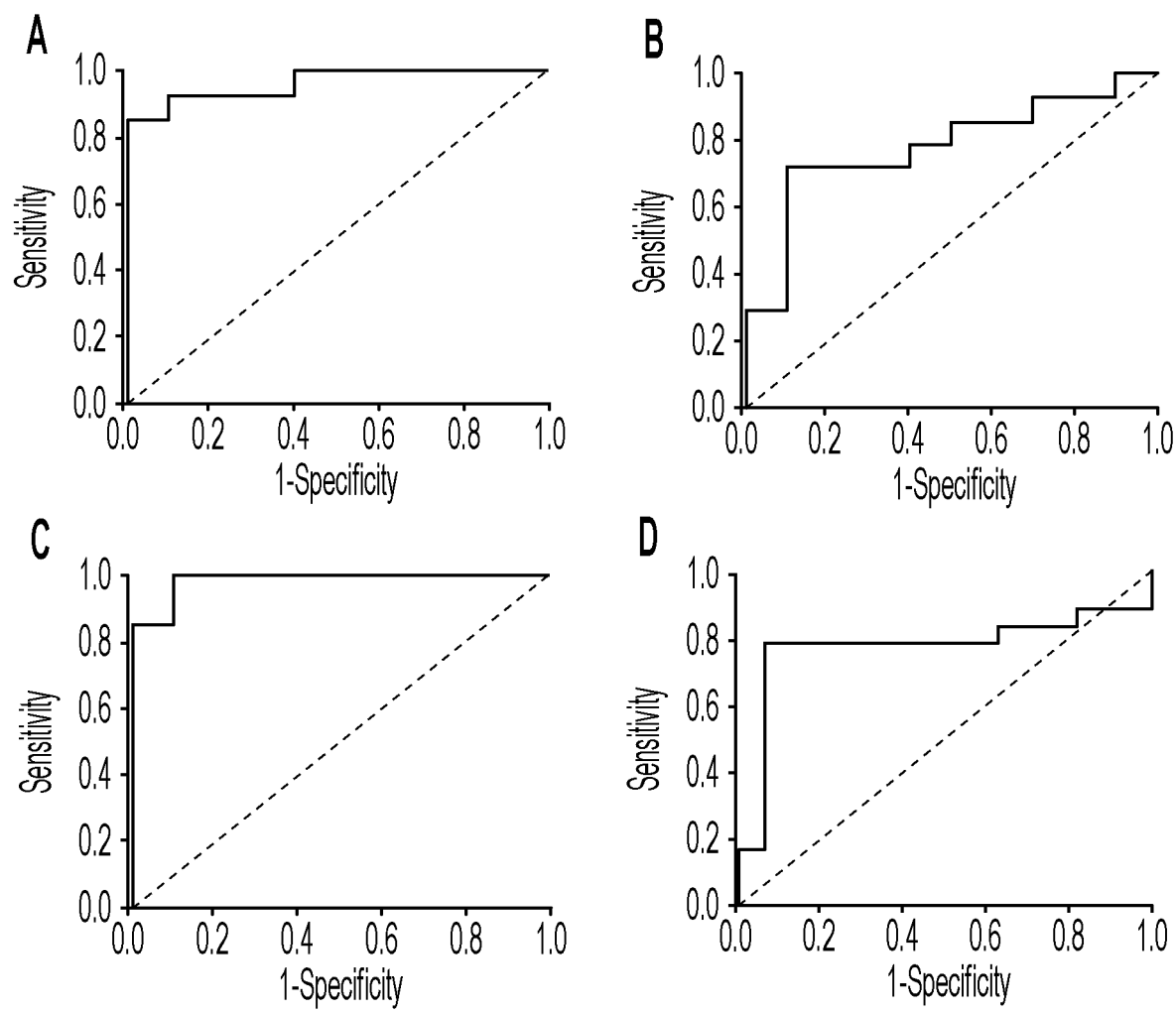

FIG. 13 shows receiver operating characteristic plots of diagnostic algorithms for detection of autistic spectrum disorder by protein glycation and oxidation adducts. (A) Algorithm-1, plasma protein adduct residues. AUROC=0.96. (B) Algorithm-2, plasma free amino acid adducts. AUROC=0.78. (C) Algorithm-3, plasma protein adduct residues and free adducts. AUROC=0.99. (D) Algorithm-4, urine free amino acid adducts. AUROC=0.78. ROC plots are representative results from one run of the classification experiment. A random outcome is AUROC=0.50.

FIG. 14 shows details of diagnostic algorithms developed for autistic spectrum disorder from plasma and urinary analytes. Algorithm outcomes for 2-fold cross-validation (10 randomized repeat trials for robustness) using SVMs (95% CI given in brackets).

FIG. 15 shows a schematic explanation for changes found in protein damage and amino acids in ASD. (A) Proposed mechanism for observed changes found in plasma protein glycation and oxidation adducts. (B) Transport of Arg and CMA across the renal tubular epithelium and proposed mechanism for increased renal CL (increased Arg and CMA reuptake). Key: grey filled arrows show processes; black-filled arrows show changes observed (A) and changes expected (B) in ASD.

FIG. 16 shows mass spectrometric multiple reaction monitoring detection of protein glycation, oxidation and nitration adducts and amino acids.

Figure 17:
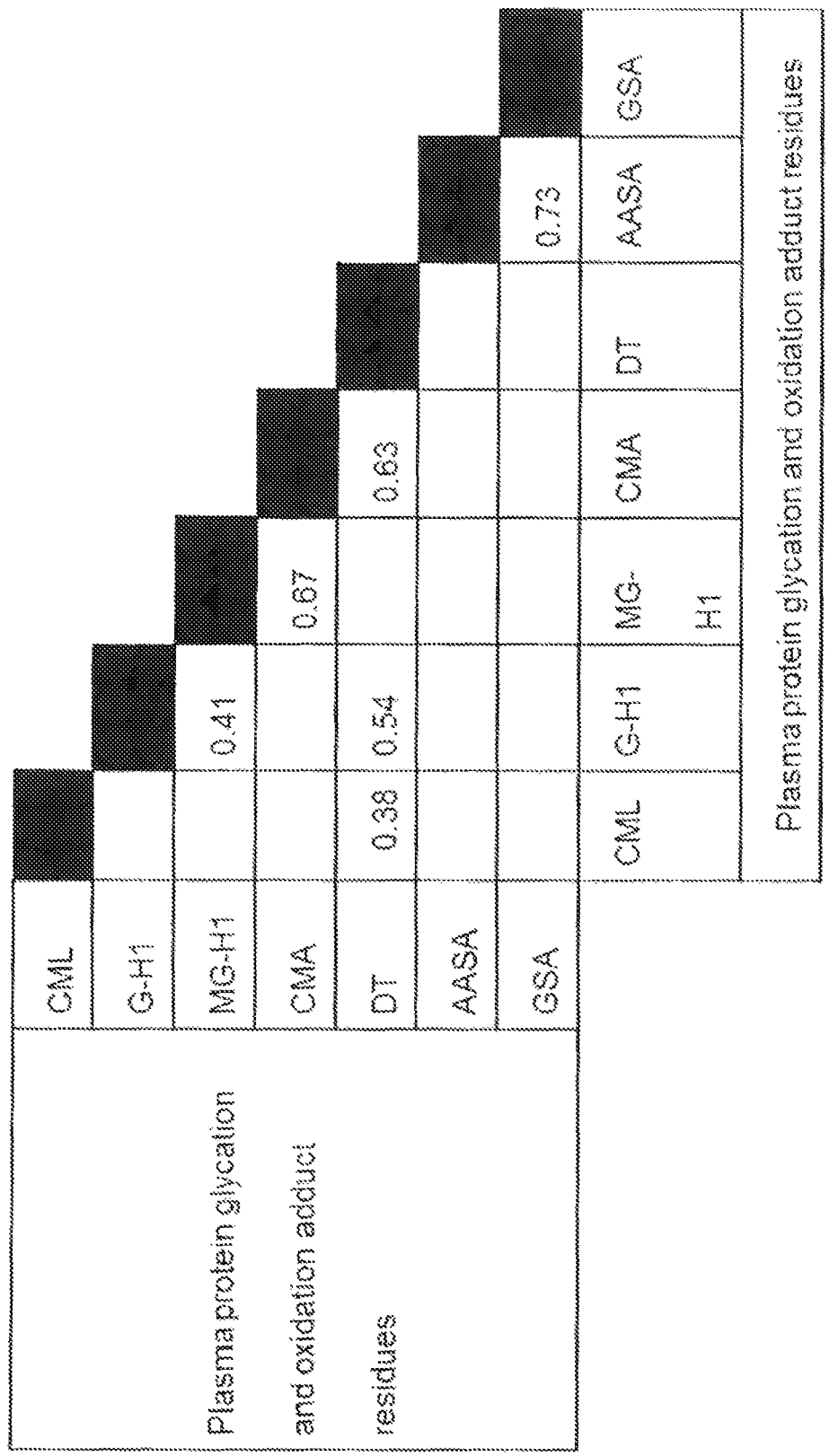

FIG. 17 shows correlation analysis of plasma protein glycation, oxidation and nitration adduct residues. Correlation coefficients; Spearman (P<0.01).

Figure 18:
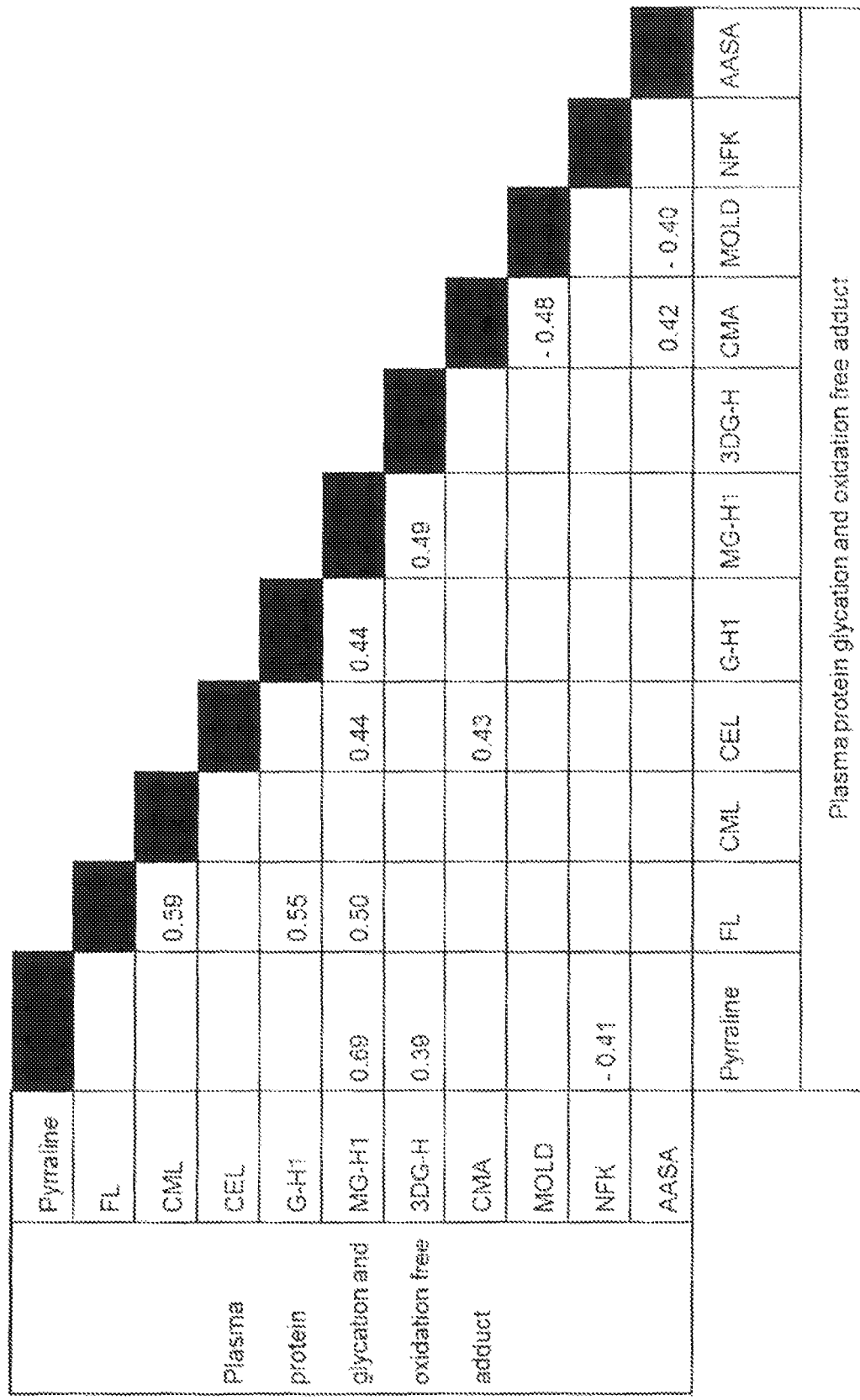

FIG. 18 shows correlation analysis of plasma protein glycation, oxidation and nitration free adducts. Correlation coefficients; Spearman (P<0.01).

Figure 19:
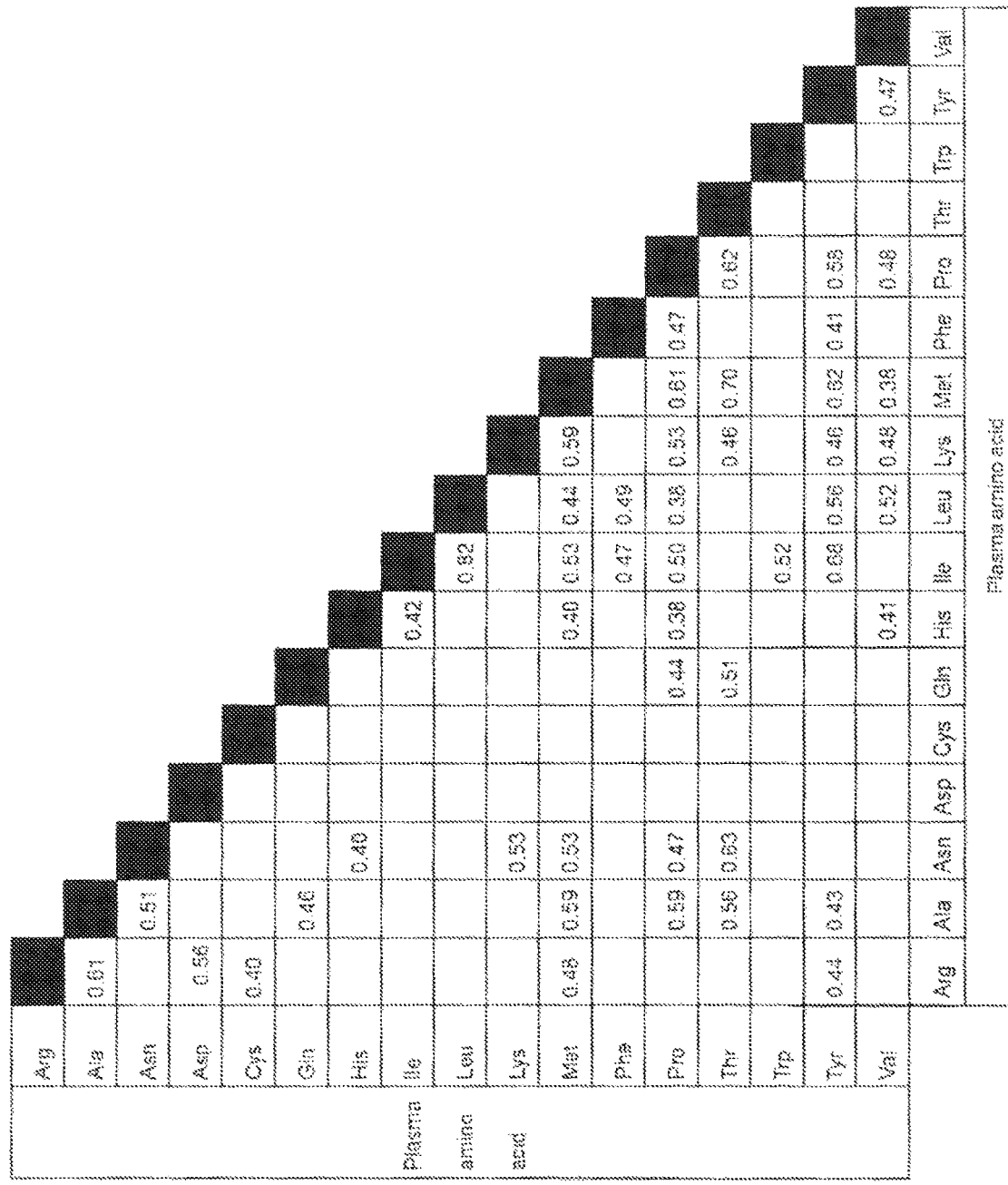

FIG. 19 shows correlation analysis of plasma amino acids. Correlation coefficients; Spearman (P<0.01).

Figure 20:
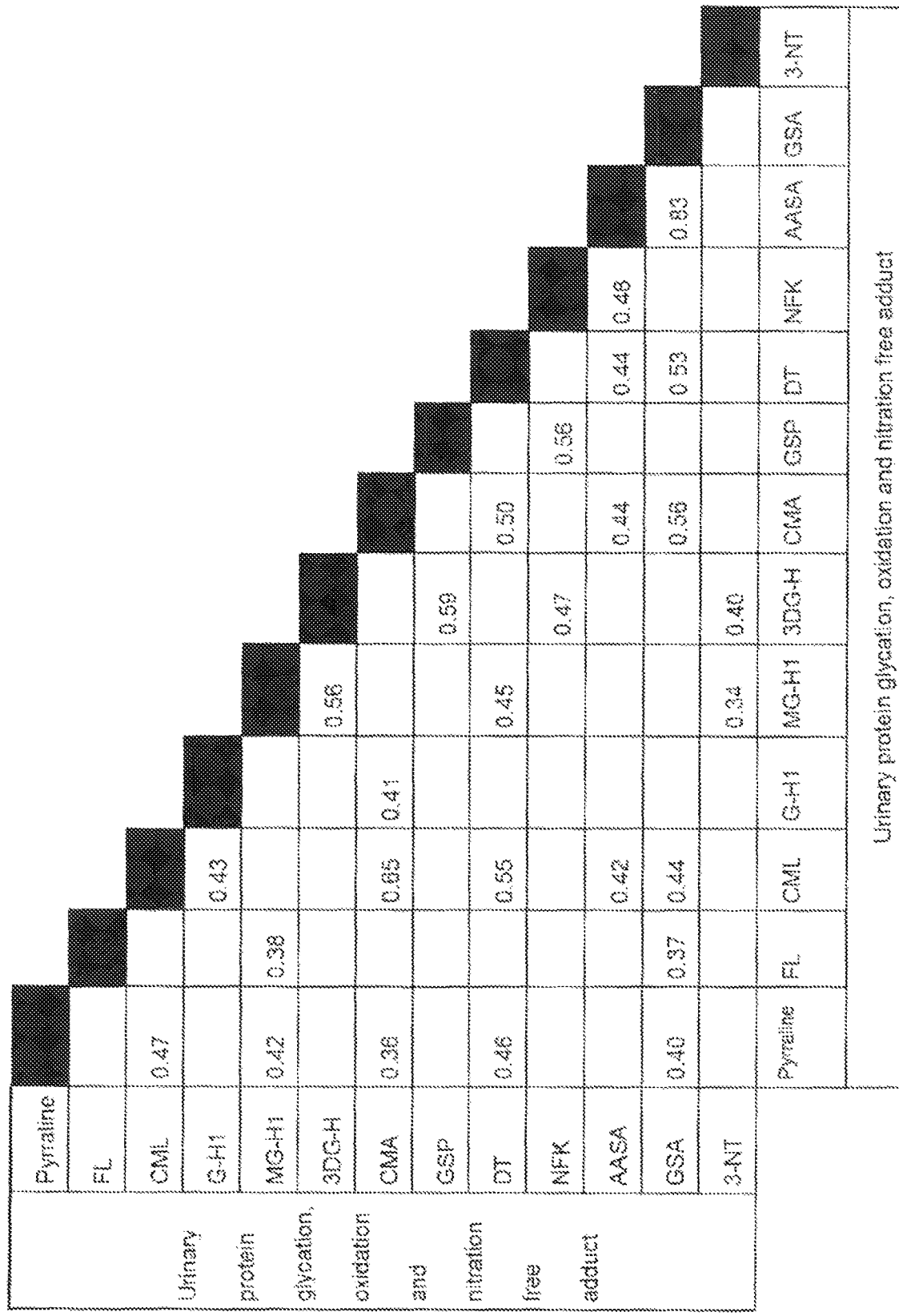

FIG. 20 shows correlation analysis of urinary protein glycation, oxidation and nitration free adducts. Correlation coefficients; Spearman (P<0.01).

Figure 21:
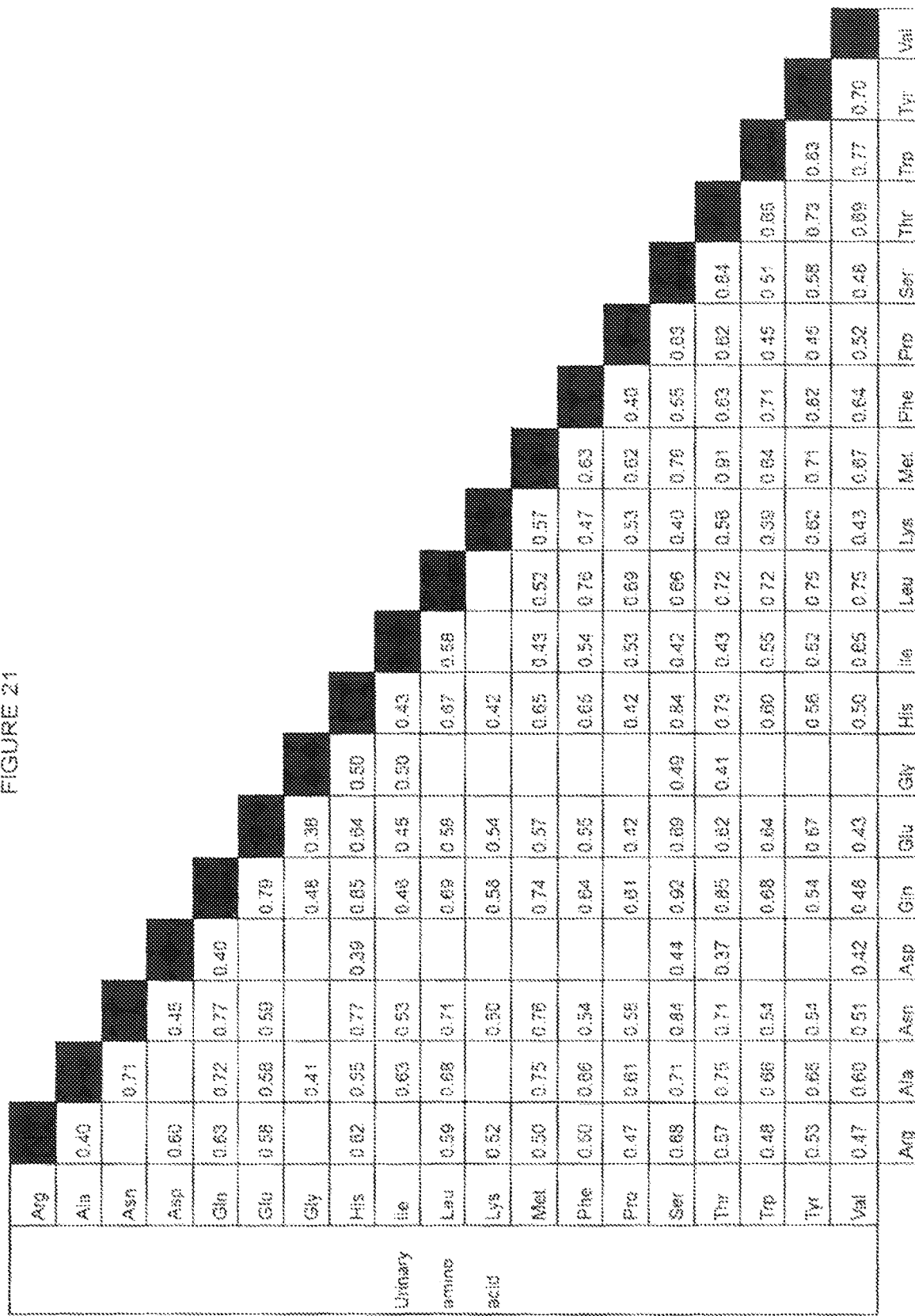

FIG. 21 shows correlation analysis of urinary amino acids. Correlation coefficients; Spearman (P<0.01).

FIG. 22 shows a confusion matrix of algorithms to identify autistic spectrum disorder. The confusion matrices shown are representative results from one run of the classification experiment.

EXAMPLES

Materials & Methods
Subject Recruitment

Figure 2:
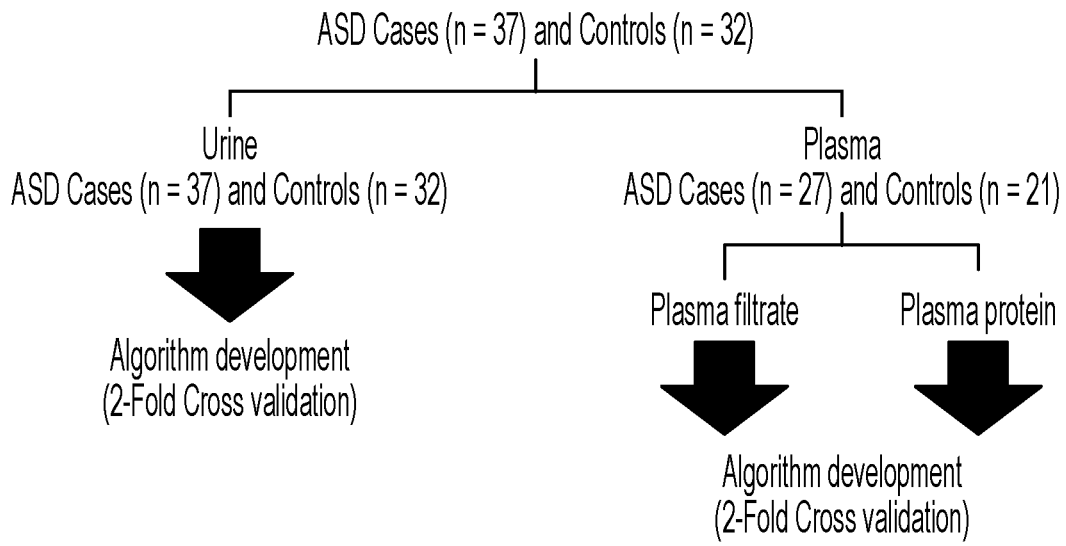
FIG. 2 shows a scheme of the training and validation subject groups of diagnostic algorithms for detection of autistic spectrum disorder.
Figure 12A:
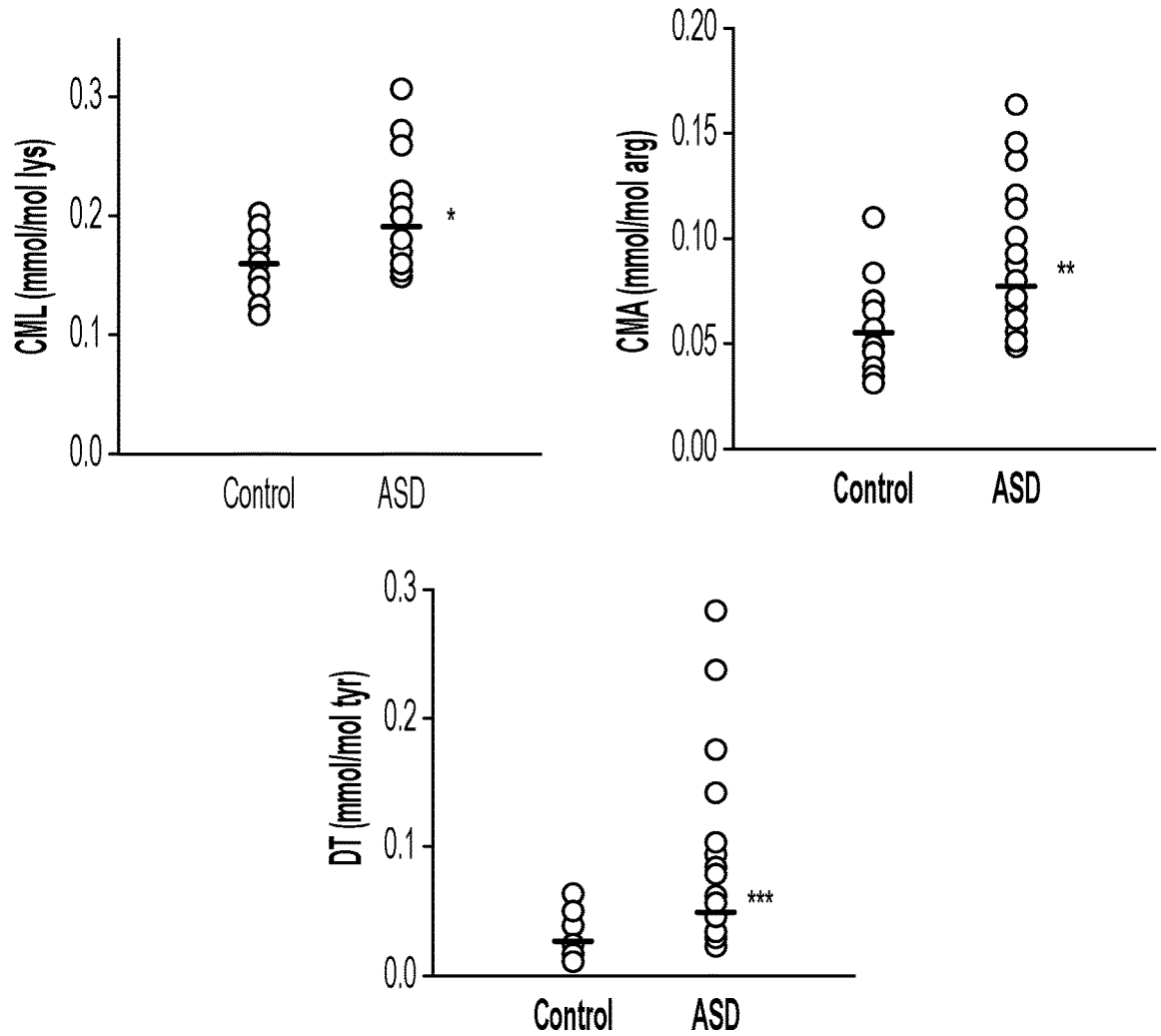
Figure 12B:
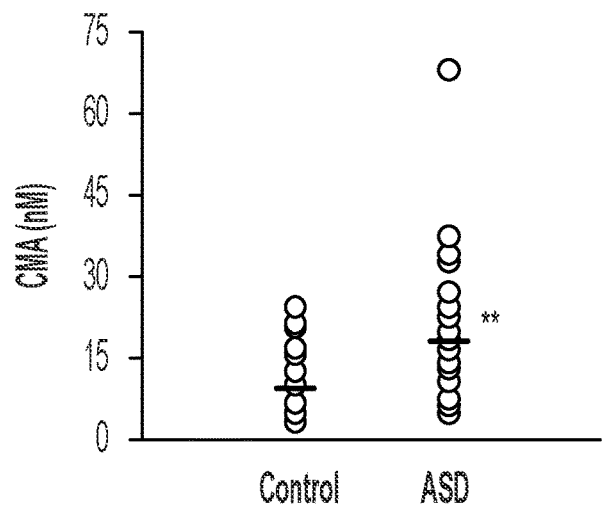
Figure 12C:
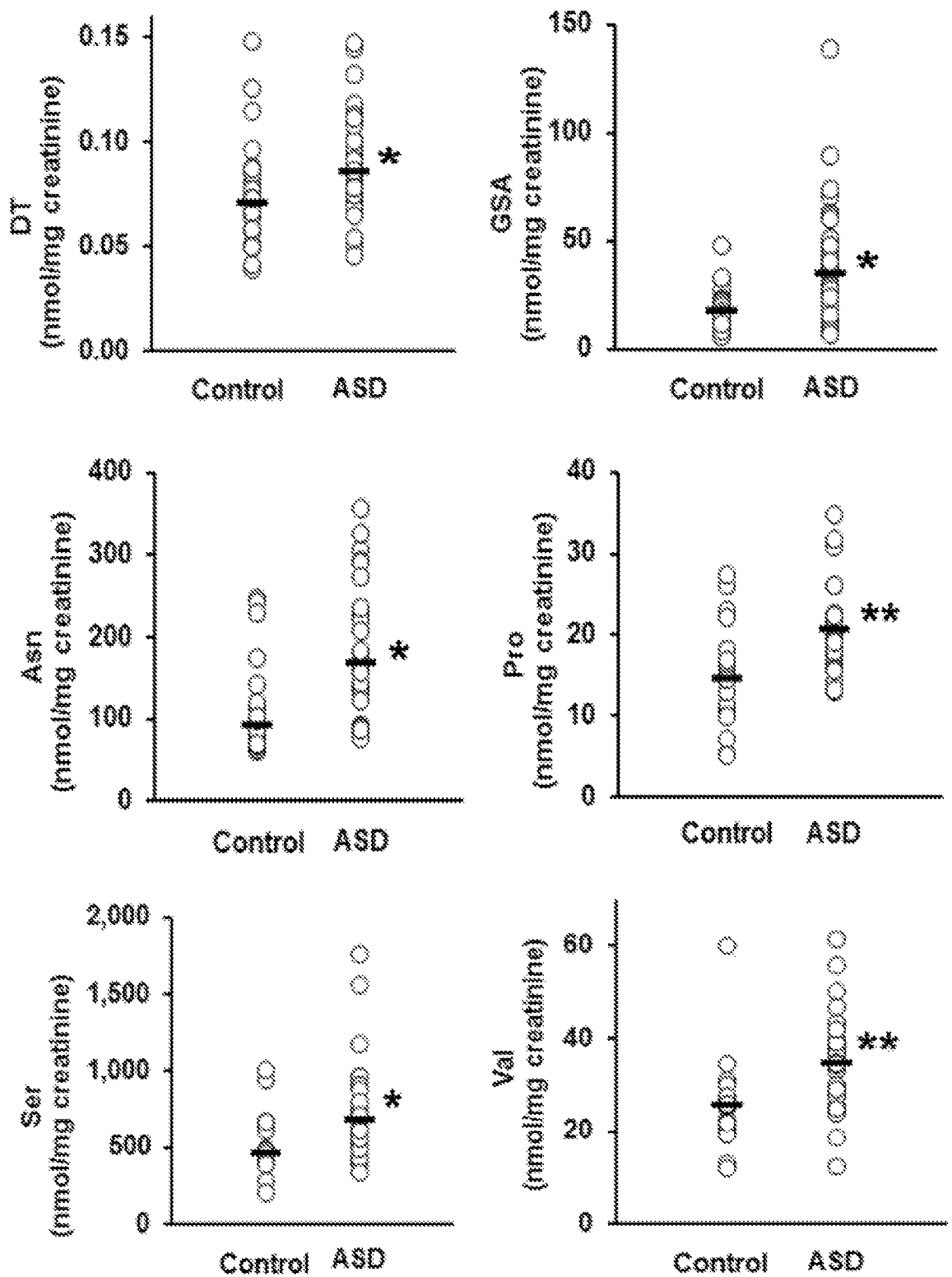
Figure 12D:
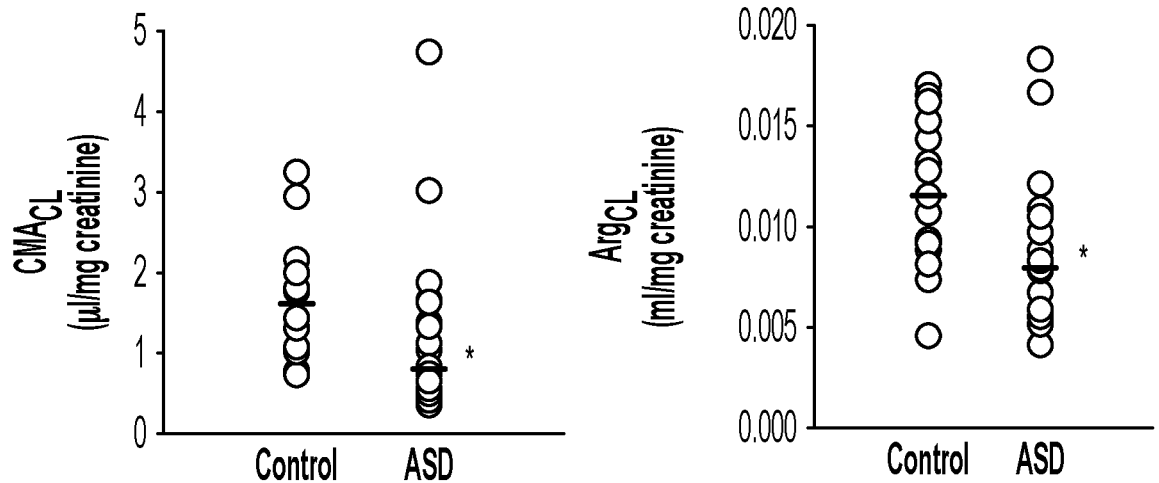

A total of 69 children were recruited. Of these, 38 had a diagnosis of ASD (29 males and 9 females) and 31 were classified as Typically Developing (TD) children (23 males and 8 females)—FIG. 2. The age of the two subject groups was not significantly different. Subject age was: ASD group, 7.6 years±2.0 years, range 5-12 years and TD group, 8.6±2.0 years, range 5-12 years. All ASD subjects received a diagnosis of ASD by two child development experts at the Child Neurology and Psychiatry Unit of the Bellaria Hospital of Bologna (IRCCS Institute of Neurological Sciences), according to the Diagnostic and Statistical Manual of Mental Disorders V (DSM 5 criteria, Autism Diagnostic Observation Schedule (ADOS), Childhood Autism Rating Scale (CARS) and characteristics of onset pattern of ASD previously defined. Developmental and cognitive levels were assessed by Psychoeducational Profile-3 (PEP-3) and Leiter International Performance Scale—Revised (Leiter-R). For both ASD and TD subjects, exclusion criteria were: presence of inflammatory or infective disease and taking antioxidant supplements at the time of study. No subject underwent any surgery intervention in the four months prior to blood and urine collection. None of the ASD subjects had active epilepsy at the time of blood and urine sampling. Subjects with ascertained medical and neurological comorbidity were excluded, through a medical work up including electroencephalography (recorded during awake and sleep), cerebral magnetic resonance imaging, standard clinical and neurological examination, neurometabolic and genetic investigations (including comparative genomic hybridization array, molecular assay for Fragile X and MECP2). Subjects recruited for this study were not taking any medication. TD children were recruited in the local community, with no sign of cognitive, learning and psychiatric involvement. They were attending mainstream school and had not been subjected to stressful events. Dietary habits were assessed by a Food Questionnaire, built according to the guidelines issued by the Emilia-Romagna Health Authority. No ASD child was on a diet free of gluten or casein. Both patients and controls were on a typical Mediterranean diet, as defined by the prevalence of both simple and complex carbohydrates, use of olive oil, and plenty of fruit. The consumption of vegetables was less than desirable in both patients and controls, although vegetable intake was more limited in ASD patients. Demographic and clinical features of ASD are summarized in FIG. 3. All subjects were recruited at the Child Neurology and Psychiatry Unit of the Bellaria Hospital of Bologna, Bologna, Italy.

Thirty-eight children with ASD were recruited for this study. The distribution of severity of ASD in this subject group recruited was (number of cases): mild (6), moderate (6) and severe (26). The distribution of cognitive/developmental impairment was (number of cases): normal/borderline IQ (11), mild (3), moderate (12) and severe (12). The distribution of onset pattern of ASD was (number of cases): early (22), regressive (6) and mixed (10). The ADOS score ranged from 13 to 22 and the CARS total score from 31.5 to 48.5.

Blood and Urine Sampling

Blood was withdrawn in the morning from fasting children. Spot urine samples were the first ones in the morning. Blood samples were collected using ethylenediaminetetraacetic acid (EDTA) as anticoagulant. Plasma and blood cells were separated immediately by centrifugation (2000 g, 10 min) and plasma samples stored at −80° C. until analysis and transferred between collaborating laboratories on dry ice.

Assay of Markers of Protein Glycation, Oxidation and Nitration

The content of glycated, oxidized and nitrated adduct residues in plasma protein was quantified in exhaustive enzymatic digests by stable isotopic dilution analysis liquid chromatography-tandem mass spectrometry (LC-MS/MS), with correction for autohydrolysis of hydrolytic enzymes. The concentrations of related glycated, oxidized and nitrated amino acid free adducts (glycated, oxidised and nitrated amino acids) in plasma and urine were determined similarly in plasma and urine ultrafiltrate, respectively. Ultrafiltrate of plasma (50 μl) was collected by microspin ultrafiltration (10 kDa cut-off) at 4° C. Retained protein was diluted with water to 500 μl and washed by 4 cycles of concentration to 50 μl and dilution to 500 μl with water over the microspin ultrafilter at 4° C. The final washed protein (100 μl) was delipidated and hydrolysed enzymatically as described (Rabbani et. al. Biochem Soc Trans. 2014; 42(2):511-7; Ahmed et. al. Sci Rep. 2015; 5:9259). Ultrafiltrate of urine (50 μl) was collected by microspin ultrafiltration (3 kDa cut-off) at 4° C.

Protein hydrolysate (25 μl, 32 μg equivalent) or ultrafiltrate (5 μl) was mixed with stable isotopic standard analytes and analysed by LC-MS/MS using an Acquity™ UPLC system with a Xevo-TQS tandem mass spectrometer (Waters, Manchester, U.K.). Samples are maintained at 4° C. in the autosampler during batch analysis. The columns were: 2.1×50 mm and 2.1 mm×250 mm, 5 μm particle size Hypercarb™ (Thermo Scientific), in series with programmed switching, at 30° C. Chromatographic retention was used to resolve oxidized analytes from their amino acid precursors to avoid interference from partial oxidation of the latter in the electrospray ionization source of the mass spectrometric detector. Analytes were detected by electrospray positive ionization and mass spectrometry multiple reaction monitoring (MRM) mode where analyte detection response was specific for mass/charge ratio of the analyte molecular ion and major fragment ion generated by collision-induced dissociation in the mass spectrometer collision cell. The ionization source and desolvation gas temperatures were 120° C. and 350° C., respectively, cone gas and desolvation gas flow rates were 99 and 900 I/h and the capillary voltage was 0.60 kV. Argon gas (5.0×10−3 mbar) was in the collision cell. For MRM detection, molecular ion and fragment ion masses and collision energies optimized to ±0.1 Da and ±1 eV, respectively, were programmed—FIG. 16.

Analytes determined were:
glycation adducts—FL, and AGEs, CML, CEL, pyrraline, CMA, G-H1, MG-H1, 3DG-H, MOLD and GSP;
oxidation adducts—DT, NFK, AASA, GSA;
nitration adduct, 3-NT; and
all major amino acids.

Oxidation, nitration and glycation adduct residues are normalised to their amino acid residue precursors and given as mmol/mol amino acid modified; and related free adducts are given in nM. Chemical structures and biochemical and clinical significance of these analytes have been described elsewhere (Thornalley & Rabbani, Biochim Biophys Acta. 2014; 1840(2):818-29; and Ahmed et. al, Sci Rep. 2015; 5(9259):9251-7). Renal clearance (CL) of glycation, oxidation and nitration free adducts and unmodified amino acids was deduced from plasma and spot urine collections: CL (μl/mg creatinine or ml/mg creatinine)=[Analyte]Urine (nmol/mg creatinine)/[Analyte]Plasma (pmol/ml or nmol/ml).

Machine Learning Analysis

The objective was to distinguish between children with ASD and healthy controls. In all cases, the diagnostic algorithms were trained on 50% of the cases and controls (training subset) before being used to predict the disease class for each sample in the remaining subjects (test set); 2-fold cross-validation. The outcome was to assign, for each test set sample, a set of probabilities corresponding to each of the ASD/control groups—the group assignment being that for which the probability is highest. Test data were held separate from algorithm training; algorithm settings were not adjusted once analysis of the test set data began—thereby guarding against overfitting and hence providing a rigorous estimate of predictive performance.

Four algorithm types were tested for performance: Random Forests, logistic regression, ensemble classifier, and Support Vector Machines (SVMs).

During the algorithm training, the complete panel of protein glycation, oxidation and nitration adducts were used as features and developed algorithms for each analyte type: plasma protein adduct residues, plasma free adducts and urinary free adducts. For the latter two, unmodified amino acids were also included as features. The aim during the training was to select the set of features that accomplishes the highest performance. The machine learning experiments were initially explored using all metabolite features. Advantageously, subsequent selection of a subset of discriminant biomarker features improved the algorithm performance (see FIG. 14). For the biomarker (e.g. amino acid adduct) selection, a sequential feature selection approach was used. The biomarker feature selection and classifier selection were made on the basis of algorithm performance defined by classification accuracy, sensitivity, specificity, area under-the-curve of the receiver operating characteristic curve (AU-ROC), positive likelihood ratio, negative likelihood ratio, positive predictive value, negative predictive value, and F-measure. For each performance metric, the mean and 95% CI was determined and reported. The algorithm training and testing was repeated 10 times, without altering the algorithm parameters, with 50% data split, to test for algorithm's robustness against any bias towards data split. Computer programs were developed using Statistics and Machine Learning Toolbox of MATLAB® (MathWorks, Inc., Natick, USA), with a linear kernel SVM and sequential minimal optimisation (SMO).

Statistical Analysis

Data are presented as mean±SD for parametric distributions and median (lower-upper quartile) for non-parametric distributions. The test for normality of data distribution applied was the Kolmogorov-Smirnov test. Significance was evaluated by Student's t-test or by Mann-Whitney U-test for parametrically or non-parametrically distributed data, respectively. Bonferroni correction was made for analysis of multiple analytes without preconceived hypothesis. Correlation analysis was performed by the Spearman's rho method with continuous variables. For clinical categorical variables with 6 categories, Spearman correlation was performed—assuming approximation to a continuous variable; for other categorical variables, significance of difference of biomarker data distributions between categories was assessed by one-way ANOVA for parametric data and Kruskal-Wallis H test. Data were analysed using SPSS, version 24.0.

For power analysis in the study design, the level of the irreversible oxidative damage marker DT in plasma protein was chosen. In healthy human subjects, plasma protein DT was 0.0287±0.0027 mmol/mol tyr (n=29) in previous studies. This study was designed to detect a 50% increase in plasma protein DT at the 0.01% significance level, for which ≥18 case and control samples were required. Post-hoc analysis revealed an 88% increase with P=0.00017, after Bonferroni correction of 14 with 27 cases and 21 controls, suggesting the study was adequately powered for this key target analyte.

Example 1

Children with Autistic Spectrum Disorder Recruited for this Study

Thirty-eight children with ASD were recruited for this study. The distribution of severity of ASD in this subject group recruited was (number of cases): mild (6), moderate (6) and severe (26). The distribution of cognitive/developmental impairment was (number of cases): normal/borderline IQ (11), mild (3), moderate (12) and severe (12). The distribution of onset pattern of ASD was (number of cases): early (22), regressive (6) and mixed (10). The ADOS score ranged from 13 to 22 and the CARS total score from 31.5 to 48.5.

Example 2

Plasma Protein Glycation, Oxidation and Nitration

In plasma protein, protein content of AGEs—CML, MG-H1 and CMA—were increased in children with ASD, with respect to healthy controls; whereas plasma protein content of AGE, 3DG-H, was decreased in children with ASD, with respect to healthy controls. Plasma protein content of the oxidative damage adduct, DT, was increased in children with ASD, with respect to healthy controls. Advantageously, changes in CML, CMA and DT remained significant after Bonferroni correction for measurement of multiple analytes (FIG. 4). In correlation analysis, highly significant positive correlations (P<0.01, Spearman) were of CML with DT, G-H1 with MG-H1 and DT, MG-H1 with CMA, CMA with DT, and AASA with GSA—FIG. 17. No correlation or association of glycation, oxidation and nitration adduct residues was found with demographic and clinical features. There was no significant difference of these variables between subject groups of different genders with and without ASD.

Example 3

Plasma Glycated, Oxidized and Nitrated Amino Acids and Amino Acid Metabolome

For glycated, oxidized and nitrated amino acid concentration in plasma, FL, G-H1 and NFK were decreased whereas CMA, AASA and GSA were increased in children with ASD, with respect to healthy controls. Advantageously, increase in CMA remained significant after Bonferroni correction (FIG. 5). In correlation analysis, highly significant positive correlations were of pyrraline with MG-H1 and 3DG-H, FL with CML, G-H1 and MG-H1, CEL with MG-H1 and CMA, MG-H1 with 3DG-H, and CMA with AASA. There were highly significant negative correlations of pyrraline with NFK, CMA with MOLD, and MOLD with AASA—FIG. 18.

For the conventional amino acid metabolome, there were increases in arg, gln, glu and thr and decrease in trp in children with ASD, with respect to healthy controls. There were many highly significant positive correlations between plasma amino acid concentrations—FIG. 19. No correlation or association of glycation, oxidation and nitration free adducts and amino acids was found with demographic and clinical features. There was no significant difference of these variables between genders Example 4

Urinary Glycated, Oxidized and Nitrated Amino Acids and Amino Acid Metabolome and Renal Clearance For the urinary flux of glycated, oxidized and nitrated amino acids, children with ASD showed increased urinary excretion of CML, G-H1, CMA, MOLD, pyrraline, DT, NFK, AASA and GSA. Advantageously, urinary excretions of DT and GSA remained significant after Bonferroni correction (FIG. 6). For the urinary flux of unmodified amino acids, children with ASD showed increased urinary excretion of all amino acids except asp, cys, lys, phe and tyr. Advantageously, increases in urinary excretion of asn, pro, ser and val remained significant after Bonferroni correction (FIG. 8). There were several highly significant positive correlations between urinary excretions of glycation, oxidation and nitration adducts and amino acids—see FIGS. 20 and 21.

Renal clearance of CMA, GSP, DT, arg, glu, leu, phe and thr were decreased and renal clearance of NFK and trp were increased in children with ASD, with respect to healthy controls. Advantageously, decreases in renal clearance of arg and CMA remained significant after Bonferroni correction: $CL_{arg}$ decreased 32% and $CL_{CMA}$ decreased 50% in children with ASD, compared to healthy control; P<0.001 (FIGS. 9 and 10). No correlation or association of these glycation, oxidation and nitration free adduct and amino acid variables was found with demographic and clinical features. There was no significant difference of these variables between genders.

Changes of glycation, oxidation and nitration adducts and amino acid metabolome in plasma and urine are summarized in heat maps (FIGS. 11A and 11B). Data distributions of biomarker (amino acid adduct and amino acid) with significantly different change in the ASD study group after Bonferroni correction are given in FIG. 12.

Example 5

Development of Diagnostic Algorithms for Autistic Spectrum Disorder

To explore diagnostic utility of protein glycation, oxidation and nitration measurements for ASD, we analysed plasma and urinary amino acid analyte data by a machine learning approach. SVMs was the best-performing method out of the four algorithms that were investigated. Algorithm optimised from 2-fold cross-validation were as below.

(i) Algorithm-1, developed from plasma protein glycation, oxidation and nitration adduct residue analytes.

It has the following features: CML, 3DG-H, CMA and DT. Classification accuracy was 88%, sensitivity 92%, specificity 84% and AUROC 0.94. A random outcome is 0.50.

(ii) Algorithm-2, developed from plasma glycated, oxidized and nitrated amino acids and conventional amino acid metabolome.

It has the following features: CML and CMA. Classification accuracy was 75%, sensitivity 81% and specificity 67% and AUROC 0.80.

(iii) Algorithm-3, developed from plasma protein glycation, oxidation and nitration adduct residues and plasma glycated, oxidized and nitrated amino acids and conventional amino acid metabolome combined.

It has the following features: plasma protein CML, 3DG-H, CMA and DT residues and plasma G-H1 and GSA free adducts. Classification accuracy was 89%, sensitivity 90%, specificity 87% and AUROC 0.95.

(iv) Algorithm-4, developed from urinary glycated, oxidized and nitrated amino acids.

It has the following features: GSA and pyrraline free adducts. Classification accuracy was 77%, sensitivity 77%, specificity 76% and AUROC 0.79 (FIGS. 13, 14 and 22).

The diagnostic algorithms were used to deduce the probability of having ASD for each patient diagnosed with ASD by clinical symptoms (FIG. 3). The association and correlation of these probabilities with clinical features was explored. No significant association or correlation of these probabilities with clinical features (age, ADOS, total CARS, CARS hyperactivity and CARS body use scores, autism severity, cognitive/developmental impairment and ASD onset pattern) was found.

Without wishing to be bound by theory, the findings of the present inventors implicate a disturbance of metabolism of dicarbonyl precursors of advanced glycation endproducts (AGEs) and activation of dual oxidase (DUOX) in ASD. The initial evidence given herein suggests detection of the combination of plasma protein AGE and dityrosine (DT) concentrations may provide an optimal blood-based test for diagnosis of ASD. Decreased renal clearance of arginine and CMA is proposed to be linked to amino acid transporter dysfunction in ASD, building on increasing evidence of neuronal amino acid availability as a driver in ASD development.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for diagnosing an autistic spectrum disorder (ASD), said method comprising:
   a. detecting the concentration of an amino acid adduct in a sample obtained from a subject, wherein said amino acid adduct is a glycated amino acid adduct, an oxidised amino acid adduct, or a nitrated amino acid adduct, and wherein the amino acid adduct is one or more selected from Nε-carboxymethyl-lysine (CML), 3-deoxyglucosone-derived hydroimidazolone (3DG-H), Nω-carboxymethylarginine (CMA), dityrosine (DT), glutamic semialdehyde (GSA), glyoxal-derived hydroimidazolone (G-H1), pyrraline, methylglyoxal-derived hydroimidazolone (MG-H1), Nε-fructosyl-lysine (FL), Nε-(1-carboxyethyl)lysine (CEL), α-aminoadipic semialdehyde (AASA), and methylglyoxal-derived lysine dimer (MOLD);
   b. comparing the concentration of the amino acid adduct in the sample with the concentration of the same amino acid adduct in a reference standard; and
   c. identifying with the presence or absence of a concentration difference of said amino acid adduct in the sample relative to the reference standard, wherein the presence or absence of a concentration difference correlates with the presence or absence of ASD.

2. The method of claim 1, said method further comprising:
   a. detecting the concentration of the amino acid adduct in the sample obtained from the subject; and
   b. classifying the health of the subject based on the concentration of the amino acid adduct detected in the sample with a diagnostic algorithm, wherein the diagnostic algorithm is trained on the corresponding concentration for the same amino acid adduct obtained from a population of subjects having known disease status, and thereby diagnosing the presence or absence of ASD in the subject.

3. A method for treating an autistic spectrum disorder (ASD), said method comprising:
   a. requesting the performance or obtaining the results of a method of claim 1; and
   b. administering to a subject diagnosed with ASD a therapy for ASD.

4. The method of claim 1, wherein steps (b) and/or (c) of claim 1 are conducted with/using a diagnostic algorithm, preferably wherein the diagnostic algorithm is configured to diagnose the presence or absence of ASD based on the concentration of the amino acid adduct detected in the sample, wherein the diagnostic algorithm is trained on the corresponding concentration for the same amino acid adduct in one or more (preferably a plurality of) reference standards, or preferably wherein the diagnostic algorithm is configured to classify the health of the subject based on the concentration of the amino acid adduct detected in the sample, wherein the diagnostic algorithm is trained on the corresponding concentration for the same amino acid adduct obtained from a population of subjects having known disease status.

5. The method of claim 1, wherein the method is for:
   a. diagnosing ASD;
   b. determining prognosis of ASD;
   c. identifying a therapy suitable for treating ASD;
   d. monitoring efficacy of an ASD therapy; and/or
   e. using an ASD diagnostic algorithm.

6. The method of claim 1, wherein the sample is selected from one or more of blood, blood plasma, blood plasma ultrafiltrate, urine, blood serum, synovial fluid and/or sputum.

7. The method of claim 1, wherein the amino acid adduct is at least two selected from Nc-carboxymethyl-lysine (CML), 3-deoxyglucosone-derived hydroimidazolone (3DG-H), Nw-carboxymethylarginine (CMA), dityrosine (DT), glutamic semialdehyde (GSA), glyoxal-derived hydroimidazolone (G-H1), pyrraline, methylglyoxal-derived hydroimidazolone (MG-H1), $N_E$-fructosyl-lysine (FL), $N_E$-(1-carboxyethyl)lysine (CEL), a-aminoadipic semialdehyde (AASA), and methylglyoxal-derived lysine dimer (MOLD).

8. The method of claim 1, wherein:
   a. the concentration of one or more amino acid adduct is selected from: CML, CMA, and GSA is the same or increased; and/or b. the concentration of one or more amino acid adduct is selected from:

3DG-H and G-H1 (free adduct) is the same or decreased; when compared to an ASD reference standard, and indicates the presence of ASD.

9. The method of claim 8, wherein the concentration of CML and/or CMA is increased when compared to a non-ASD reference standard or an ASD reference standard, and indicates the presence of ASD.

10. The method of claim 8, wherein the sample is a blood sample.

11. The method of claim 8, wherein the concentration of GSA and/or pyrraline is increased when compared to a non-ASD reference standard or an ASD reference standard, and indicates the presence of ASD.

12. The method of claim 1, wherein the sample is a urine sample.

13. The method of claim 1, wherein the amino acid adduct is detected by stable isotopic dilution analysis liquid chromatography-tandem mass spectrometry reaction monitoring (SRM) mass spectrometry, Western Blot, Enzyme-Linked Immunosorbent Assay (ELISA), liquid chromatography mass spectrometry (LC-MS), reverse phase mass spectrometry, surface enhanced laser desorption ionisation time-of-flight mass spectrometry (SELDI-TOF), matrix assisted laser desorption ionisation time-of-flight mass spectrometry (MALDI-TOF), liquid chromatography-tandem mass spectrometry, isotope dilution mass spectrometry, size permeation (gel filtration), ion exchange, affinity, high performance liquid chromatography, ultra performance liquid chromatography, one-dimensional gel electrophoresis (1-DE), and/or two-dimensional gel electrophoresis (2-DE).

14. The method of claim 13, wherein the amino acid adduct is detected by mass spectroscopy.

15. The method of claim 13, wherein the amino acid adduct is detected by liquid chromatography-tandem mass spectrometry.

16. The method of claim 1, wherein the autistic spectrum disorder is selected from one or more of autism, Asperger syndrome, pervasive developmental disorder not otherwise specified (PDD-NOS), and childhood disintegrative disorder.

17. The method of claim 1, further comprising the step of recording on a suitable data carrier, the data obtained in the step of detecting the concentration of an amino acid adduct in a sample.

18. The method of claim 5, further comprising using a kit comprising reagents for detecting the concentration of the amino acid adduct in the sample; and instructions for use of the same.

* * * * *